US008463346B2

(12) United States Patent
Kuhn et al.

(10) Patent No.: US 8,463,346 B2
(45) Date of Patent: Jun. 11, 2013

(54) ABSOLUTE CALIBRATED TISSUE OXYGEN SATURATION AND TOTAL HEMOGLOBIN VOLUME FRACTION

(75) Inventors: Jonathan L. Kuhn, Ham Lake, MN (US); David A. Anderson, Stanchfield, MN (US); Can Cinbis, Shoreview, MN (US); Richard J. O'Brien, Hugo, MN (US); Yong K. Cho, Maple Grove, MN (US); Thomas J. Mullen, Andover, MN (US); Avram Scheiner, Vadnais Heights, MN (US); Rodolphe P. Katra, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 272 days.

(21) Appl. No.: 12/797,800

(22) Filed: Jun. 10, 2010

(65) Prior Publication Data

US 2010/0317940 A1 Dec. 16, 2010

Related U.S. Application Data

(60) Provisional application No. 61/185,824, filed on Jun. 10, 2009.

(51) Int. Cl.
*A61B 5/00* (2006.01)

(52) U.S. Cl.
USPC .......... 600/323; 600/322; 600/328; 600/331; 600/333

(58) Field of Classification Search
CPC ....................................................... A61B 5/00
USPC .......................... 600/323; 607/5, 6, 122, 322
See application file for complete search history.

(56) References Cited

U.S. PATENT DOCUMENTS

| 4,180,078 A | 12/1979 | Anderson |
| 4,202,339 A | 5/1980 | Wirtzfeld et al. |
| 4,230,122 A | 10/1980 | Lubbers et al. |
| 4,399,820 A | 8/1983 | Wirtzfeld et al. |

(Continued)

FOREIGN PATENT DOCUMENTS

| EP | 760476 | 3/1997 |
| EP | 1764034 | 3/2007 |

(Continued)

OTHER PUBLICATIONS

Hedberg, Sven-Erik, Implantable Medical Device, Oct. 2, 2008, WO2008118042.*

(Continued)

*Primary Examiner* — Clayton E LaBalle
*Assistant Examiner* — Kevin Butler
(74) *Attorney, Agent, or Firm* — Evan M. Mburu

(57) ABSTRACT

A medical device for monitoring a patient condition includes a sensor capable of being advanced transvascularly to be positioned along a volume of tissue, the sensor including a first combination of a light source and a light detector to emit light into a volume of tissue and to detect light scattered by the volume of tissue and to generate a first output signal corresponding to an intensity of the detected light. A control module is coupled to the light source to control the light source to emit light at least four spaced-apart light wavelengths, and a monitoring module is coupled to the light detector to receive the output signal and compute a measure of tissue oxygenation using the light detector output signal.

26 Claims, 11 Drawing Sheets

U.S. PATENT DOCUMENTS

| | | | |
|---|---|---|---|
| 4,467,807 A | 8/1984 | Bornzin | |
| 4,548,209 A | 10/1985 | Wielders et al. | |
| 4,567,892 A | 2/1986 | Picchi et al. | |
| 4,750,495 A | 6/1988 | Moore et al. | |
| 4,967,748 A * | 11/1990 | Cohen | 607/6 |
| 5,007,423 A * | 4/1991 | Branstetter et al. | 600/334 |
| 5,163,427 A | 11/1992 | Keimel | |
| 5,176,137 A | 1/1993 | Erickson et al. | |
| 5,188,105 A | 2/1993 | Keimel | |
| 5,188,108 A * | 2/1993 | Secker | 600/310 |
| 5,193,535 A | 3/1993 | Bardy et al. | |
| 5,213,098 A | 5/1993 | Bennett | |
| 5,218,962 A * | 6/1993 | Mannheimer et al. | 600/331 |
| 5,227,181 A * | 7/1993 | Knudsen | 425/549 |
| 5,354,316 A | 10/1994 | Keimel | |
| 5,364,316 A | 11/1994 | Brambilla | |
| 5,385,143 A * | 1/1995 | Aoyagi | 600/310 |
| 5,398,680 A | 3/1995 | Polson et al. | |
| 5,431,172 A | 7/1995 | Hoegnelid et al. | |
| 5,464,434 A | 11/1995 | Alt | |
| 5,470,345 A | 11/1995 | Hassler et al. | |
| 5,531,714 A * | 7/1996 | Dahn et al. | 604/264 |
| 5,545,186 A | 8/1996 | Olson et al. | |
| 5,588,427 A | 12/1996 | Tien | |
| 5,593,431 A | 1/1997 | Sheldon | |
| 5,596,986 A | 1/1997 | Goldfarb | |
| 5,683,432 A | 11/1997 | Goedeke et al. | |
| 5,725,219 A | 3/1998 | Gilbert | |
| 5,752,519 A | 5/1998 | Benaron et al. | |
| 5,769,785 A | 6/1998 | Diab et al. | |
| 5,855,593 A | 1/1999 | Olson et al. | |
| 5,879,294 A | 3/1999 | Anderson et al. | |
| 5,902,326 A | 5/1999 | Lessar et al. | |
| 6,144,866 A | 11/2000 | Miesel et al. | |
| 6,198,952 B1 | 3/2001 | Miesel et al. | |
| 6,226,540 B1 * | 5/2001 | Bernreuter | 600/323 |
| 6,236,882 B1 | 5/2001 | Lee et al. | |
| 6,292,698 B1 | 9/2001 | Duffin et al. | |
| 6,377,840 B1 | 4/2002 | Gritsenko et al. | |
| 6,473,632 B1 * | 10/2002 | Myers | 600/322 |
| 6,481,899 B1 | 11/2002 | Quast et al. | |
| 6,487,343 B1 | 11/2002 | Lewandowski et al. | |
| 6,512,940 B1 | 1/2003 | Brabec et al. | |
| 6,522,915 B1 | 2/2003 | Ceballos et al. | |
| 6,599,250 B2 | 7/2003 | Webb et al. | |
| 6,615,064 B1 | 9/2003 | Aldrich | |
| 6,622,046 B2 | 9/2003 | Fraley et al. | |
| 6,667,803 B1 | 12/2003 | Flessland et al. | |
| 6,682,135 B1 | 1/2004 | Zheng | |
| 6,738,667 B2 | 5/2004 | Deno et al. | |
| 6,839,583 B1 | 1/2005 | Lewandowski et al. | |
| 6,839,592 B2 | 1/2005 | Grandjean | |
| 6,850,787 B2 | 2/2005 | Weber et al. | |
| 6,892,006 B2 | 5/2005 | Lewandowski et al. | |
| 6,944,488 B2 | 9/2005 | Roberts | |
| 6,997,879 B1 | 2/2006 | Turcott | |
| 7,043,294 B1 | 5/2006 | Paris | |
| 7,096,064 B2 | 8/2006 | Deno et al. | |
| 7,164,948 B2 | 1/2007 | Struble et al. | |
| 7,165,893 B2 | 1/2007 | Schmitz | |
| 7,177,686 B1 | 2/2007 | Turcott | |
| 7,239,385 B2 | 7/2007 | Schmitz et al. | |
| 7,239,901 B2 | 7/2007 | Gritsenko | |
| 7,277,757 B2 | 10/2007 | Casavant et al. | |
| 7,302,294 B2 | 11/2007 | Kamath et al. | |
| 7,536,214 B2 * | 5/2009 | Myers et al. | 600/323 |
| 7,613,489 B2 * | 11/2009 | Myers | 600/323 |
| 7,809,441 B2 | 10/2010 | Kane et al. | |
| 7,813,778 B2 * | 10/2010 | Benaron et al. | 600/323 |
| 7,991,448 B2 | 8/2011 | Edgar, Jr. et al. | |
| 8,038,626 B2 | 10/2011 | Cinbis et al. | |
| 8,055,321 B2 | 11/2011 | Bernreuter | |
| 8,090,432 B2 | 1/2012 | Cinbis et al. | |
| 8,165,662 B2 | 4/2012 | Cinbis et al. | |
| 2003/0004412 A1 * | 1/2003 | Izatt et al. | 600/425 |
| 2003/0144584 A1 * | 7/2003 | Mendelson | 600/323 |
| 2003/0187480 A1 | 10/2003 | KenKnight et al. | |
| 2003/0199956 A1 | 10/2003 | Struble et al. | |
| 2004/0024297 A1 * | 2/2004 | Chen et al. | 600/323 |
| 2004/0220629 A1 | 11/2004 | Kamath et al. | |
| 2005/0119586 A1 | 6/2005 | Coyle et al. | |
| 2005/0148832 A1 | 7/2005 | Reghabi et al. | |
| 2005/0277818 A1 * | 12/2005 | Myers | 600/323 |
| 2006/0009685 A1 * | 1/2006 | Finarov et al. | 600/310 |
| 2006/0106293 A1 | 5/2006 | Fantini | |
| 2006/0253007 A1 | 11/2006 | Cheng et al. | |
| 2007/0093701 A1 * | 4/2007 | Myers et al. | 600/323 |
| 2007/0239052 A1 | 10/2007 | Bhunia | |
| 2007/0239053 A1 | 10/2007 | Bhunia | |
| 2007/0239215 A1 | 10/2007 | Bhunia et al. | |
| 2007/0255148 A1 | 11/2007 | Bhunia | |
| 2008/0004513 A1 | 1/2008 | Walker et al. | |
| 2008/0015424 A1 | 1/2008 | Bernreuter | |
| 2008/0103538 A1 | 5/2008 | Walker et al. | |
| 2008/0208020 A1 | 8/2008 | Cinbis et al. | |
| 2008/0208269 A1 | 8/2008 | Cinbis et al. | |
| 2008/0306390 A1 | 12/2008 | Cinbis | |
| 2010/0185252 A1 | 7/2010 | Bjorling et al. | |
| 2010/0292548 A1 | 11/2010 | Baker, Jr. et al. | |
| 2010/0317943 A1 | 12/2010 | Kuhn et al. | |
| 2011/0066017 A1 | 3/2011 | Kuhn | |
| 2011/0205535 A1 * | 8/2011 | Soller et al. | 356/300 |
| 2012/0116487 A1 * | 5/2012 | Burnett et al. | 607/105 |
| 2013/0023744 A1 * | 1/2013 | Benni | 600/339 |

FOREIGN PATENT DOCUMENTS

| | | |
|---|---|---|
| EP | 1955653 | 8/2008 |
| GB | 1419701 | 12/1975 |
| WO | 9825669 | 6/1998 |
| WO | 0377750 | 9/2003 |
| WO | 2004091719 | 10/2004 |
| WO | 2007012931 | 2/2007 |
| WO | 2008105698 | 9/2008 |
| WO | 2008118042 | 10/2008 |
| WO | WO2008118042 A1 * | 10/2008 |
| WO | 2008151263 | 12/2008 |

OTHER PUBLICATIONS

Myers, Dean E., Noninvasive Method for Measuring Local Hemoglobin Oxygen Saturation in Tissue Using Wide Gap Second Derivative Near-Infrared Spectroscopy, Journal of Biomedical Optics 10(3), 034017 (May/Jun. 2005).

Benaron, David A., Quantitative Clinical Non-Pulsatile and Localized Visible Light Oximter: Design of the T-Stat (Trade Market) Tissue Oximeter, Stanford University School of Medicine, Palo Alto, CA USA 94305.

(PCT/US2010/038111) PCT Notification of Transmittal of the International Search Report and the Written Opinion of the International Searching Authority, Mailed Sep. 20, 2010, 9 pages.

St Jude Medical, ME 317: Design for Manufacturability, Implantable Pulse Generator Optical Sensing System, Jun. 1, 2004, 225 pages.

M.N. Ericson et al., Development of an Implantable Oximetry-Based Organ Perfusion Sensor, Proceeding of the 26th Annual International Conference of the IEEE EMBS, Sep. 1-5, 2004, pp. 2235-2238.

Jr Wilson et al., Noninvasive Detection of Skeletal Muscle Underperfusion with Near-Infrared Spectroscopy ion Patients with Heart Failure; Circulation: Journal of the American Heart Association, 1989;80; pp. 1668-1674.

* cited by examiner

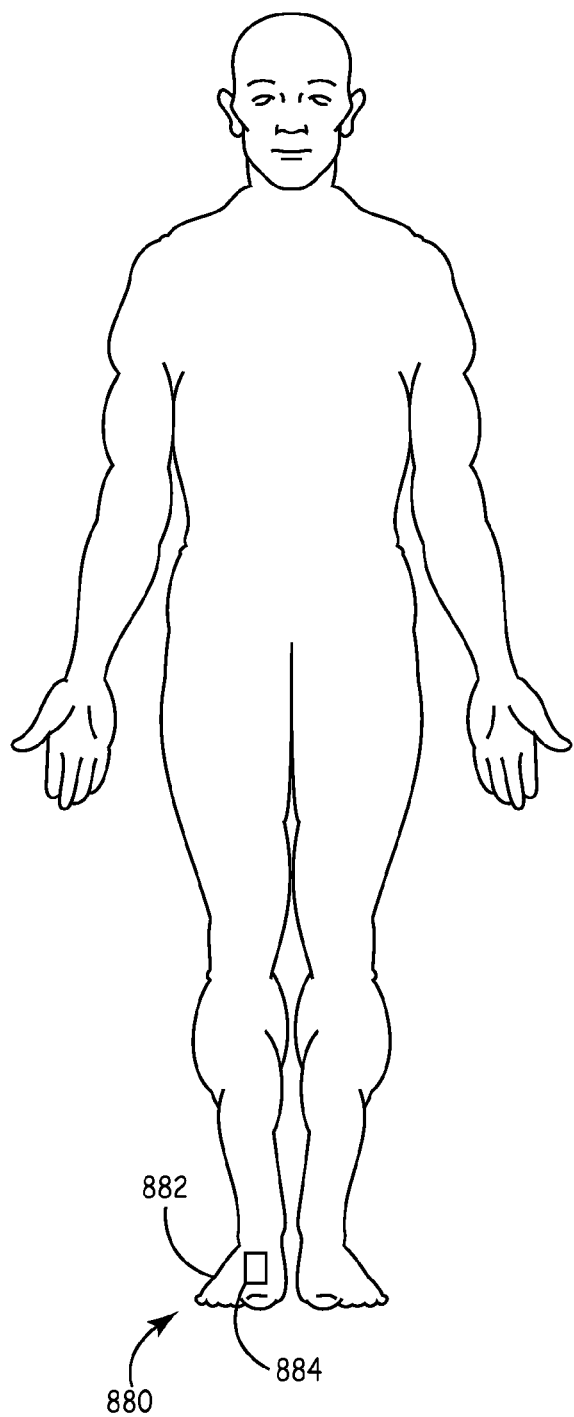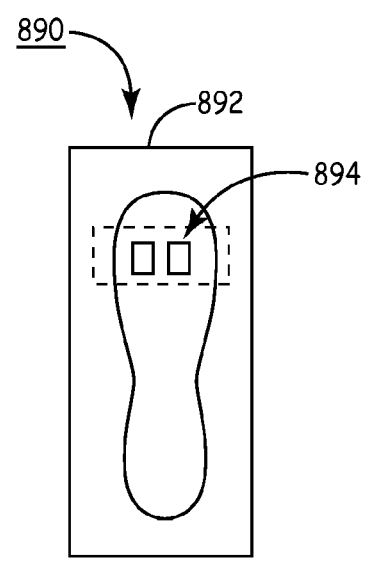
FIG. 14A
FIG. 14B

US 8,463,346 B2

ABSOLUTE CALIBRATED TISSUE OXYGEN SATURATION AND TOTAL HEMOGLOBIN VOLUME FRACTION

RELATED APPLICATION

The present disclosure claims priority and other benefits from U.S. Provisional Patent Application Ser. No. 61/185,824, filed Jun. 10, 2009, entitled "ABSOLUTE CALIBRATED TISSUE OXYGEN SATURATION AND TOTAL HEMOGLOBIN VOLUME FRACTION", incorporated herein by reference in its entirety

REFERENCE TO RELATED APPLICATIONS

Cross-reference is hereby made to the commonly-assigned related U.S. application Ser. Nos. 12/797,736, 12/797,744 and 12/797,770, all entitled "DEVICE AND METHOD FOR MONITORING ABSOLUTE OXYGEN SATURATION AND TOTAL HEMOGLOBIN CONCENTRATION", to Kuhn et al.; Ser. Nos. 12/797,815, 12/797,816 and 12/797,823 all entitled "TISSUE OXYGENATION MONITORING IN HEART FAILURE" to Cinbis et al.; Ser. Nos 12/797,831, entitled "ACTIVE NOISE CANCELLATION IN AN OPTICAL SENSOR SIGNAL", to Kuhn et al.,; Ser. Nos. 12/797,781 and 12/797,793, both entitled "SHOCK REDUCTION USING ABSOLUTE CALIBRATED TISSUE OXYGEN SATURATION AND TOTAL HEMOGLOBIN VOLUME FRACTION", to Kuhn et al.; and Ser. No. 12/797,811, entitled "ABSOLUTE CALIBRATED TISSUE OXYGEN SATURATION AND TOTAL HEMOGLOBIN VOLUME FRACTION", to Kuhn et al., all of which are incorporated herein by reference in their entireties.

TECHNICAL FIELD

The invention relates generally to medical devices and, in particular, to a medical device and associated methods for monitoring tissue oxygen availability.

BACKGROUND

A wide range of normal and pathological conditions can alter the blood and oxygen supply to body tissue. Such conditions can be systemic, affecting the whole body, or localized, affecting a portion of the body, i.e., a particular region or organ(s) of the body. Such conditions can relate to the hemoglobin content of the blood, respiratory function, metabolic demand of the particular body tissue, and pathological conditions or diseases such as heart failure, hypertension, diabetes, vascular disease, etc.

Bedside monitoring devices are available for measuring the oxygen saturation of the blood, e.g., pulse oximeters, or a localized area of tissue. However, a need remains for improved sensors and methods for monitoring the oxygenation status of body tissue for tracking patient status and managing and optimizing therapies.

BRIEF DESCRIPTION OF THE DRAWINGS

FIGS. 14A and 14B illustrate other configurations of external tissue oxygenation sensing devices.

DETAILED DESCRIPTION

Figure 1:
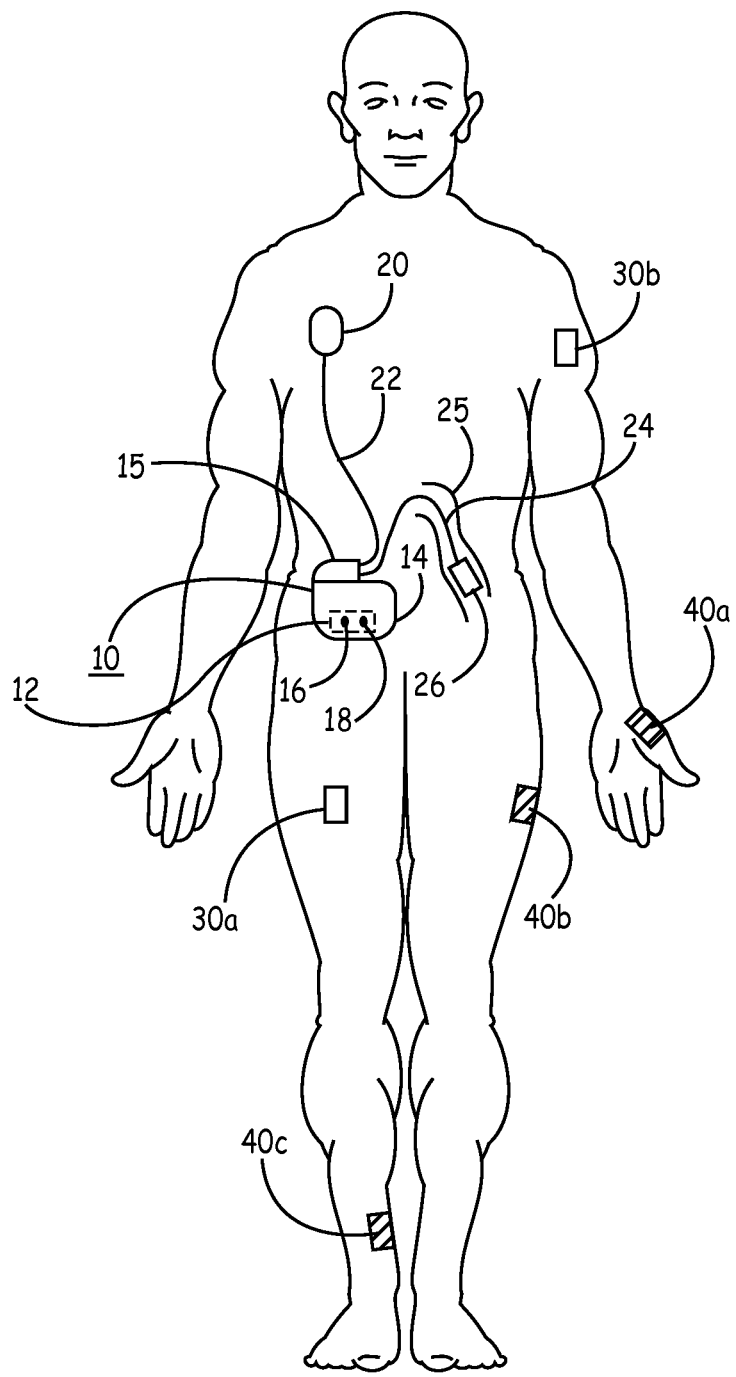
FIG. 1 is a schematic drawing of an implantable medical device (IMD) configured for monitoring tissue oxygenation in a patient.

In the following description, references are made to illustrative embodiments. It is understood that other embodiments may be utilized without departing from the scope of the invention. In some instances, for purposes of clarity, the same reference numbers may be used in the drawings to identify similar elements. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

In various embodiments described herein, an optical sensor is used to monitor tissue oxygenation in a measurement tissue volume for detecting or predicting tissue hypoxia. The measurement volume is the volume of tissue (including blood) in the optical path of the sensor. The term "tissue oxygenation" as used herein refers to the availability of oxygen to a localized tissue volume and thus refers generally to the availability of oxygenated hemoglobin.

The term "total hemoglobin volume fraction" (HbT) refers to the concentration of red blood cells in a measurement volume carrying hemoglobin and thus relates to the total hemoglobin concentration as a fraction of a measurement volume. Stated differently, the total hemoglobin volume fraction, which can be expressed as a percentage, is the volume percentage of red blood cells carrying oxygenated and deoxygenated hemoglobin in the measurement volume. Thus a measurement of HbT will include contributions from red blood cells present in any arteries, capillaries, and veins which may be present in the measurement volume. Generally speaking, when the availability of oxygen to a body tissue is being monitored, the optical sensor is positioned such that the measurement volume extends through a relatively uniform tissue volume such that optical sensor signals used to compute measurements of tissue oxygenation correlate to the absolute tissue oxygen saturation and HbT in the microcirculation of the measurement volume.

Absolute tissue oxygen saturation ($O_2$Sat) is the portion (or percentage) of the total hemoglobin that is in an oxygenated state. More specifically, $O_2$Sat relates to the available hemoglobin binding sites holding an oxygen molecule. Measurements of $O_2$Sat will be correlated to a direct measurement of tissue oxygen partial pressure ($pO_2$). "Tissue oxygenation monitoring" as used herein refers to monitoring at least one or both of $O_2$Sat (or an index thereof) and HbT (or an index thereof). Tissue oxygenation monitoring may involve determining absolute measurements of $O_2$Sat and HbT or determining trends of these measurements or trends of indices of these measurements. When either $O_2$Sat or HbT are reduced, a blood-perfused tissue can become hypoxic.

The term "hypoxia" as used herein refers to a reduced availability of oxygen to the tissue. Ischemia is a deficiency of blood flow to a body tissue due to functional constriction or actual obstruction of blood vessels to the tissue. Ischemia will lead to tissue hypoxia if the duration of the ischemic episode prevents replenishment of the oxygen supply before the tissue oxygen partial pressure becomes significantly reduced. Tissue hypoxia may also occur when the arterial blood is inadequately oxygenated. Inadequate oxygenation of the arterial blood itself is referred to as "hypoxemia." Tissue hypoxia caused by hypoxemia is referred to as "hypoxic hypoxia". Inadequate tissue oxygenation may also result from anemia, when the oxygen carrying capacity of the blood is reduced due to a deficiency of red blood cells, less than normal hemoglobin content or altered hemoglobin constituents. Hypoxia due to a reduction of the oxygen carrying capacity of the blood is referred to as "anemic hypoxia". Other forms of hypoxia include "stagnant hypoxia," which occurs when inadequate blood flow fails to transport sufficient oxygen to the tissue, such as in heart failure. As such, stagnant hypoxia generally occurs when tissue perfusion is low, e.g., due to low cardiac output.

Tissue hypoxia or anoxia (absence of oxygen) could be determined by a direct measurement of tissue oxygen partial pressure ($pO_2$). However, measurements of light scattering by blood chromophores allows measurement of $O_2$Sat and HbT in the capillary, arterial and venous blood volumes present in the measurement tissue volume to provide an indication of the availability of oxygen to the tissue. If the availability of oxygen is decreased due to any change in $O_2$Sat and/or HbT, tissue hypoxia may occur or already be present. As such, measurements of $O_2$Sat and HbT can be used to detect or predict tissue hypoxia without directly measuring the partial pressure of oxygen in the tissue. As used herein, "detection" of tissue hypoxia, therefore, refers to detecting a change in the availability of oxygen to the tissue (i.e., changes in $O_2$Sat and/or HbT) that could lead to, or has already caused, tissue hypoxia. In other words, detection of tissue hypoxia may be made before the tissue becomes hypoxic and is thus a prediction that tissue hypoxia will occur if the oxygen availability is not improved.

Monitoring absolute $O_2$Sat and HbT allows for the oxygen availability to the tissue to be determined and may allow for discrimination between different physiological conditions. As will be described herein, tissue oxygenation monitoring applications may include chronic or acute ambulatory monitoring of tissue using an implantable or wearable medical device including an optical sensor. As used herein, "chronic" monitoring generally refers to monitoring a tissue for more than one day using continuous or periodic measurements while "acute" monitoring generally refers to monitoring a tissue for one day or less, for example, testing performed during a clinical visit or measurements performed during a surgical procedure.

FIG. 1 is a schematic drawing of an implantable medical device (IMD) 10 configured for monitoring tissue oxygenation in a patient. IMD 10 may be embodied as any of a number of implantable medical devices, including pacemakers, implantable cardioverter defibrillators (ICDs), nerve stimulators, fluid delivery pumps, hemodynamic monitors, ECG monitors, or the like. In one embodiment, IMD 10 includes an optical sensor 12 incorporated in hermetically-sealed housing 14 of IMD 10. Housing 14 encloses an IMD battery and other device circuitry and components and includes at least one opening or window 16 through which light is emitted from a light emitting portion of the optical sensor 12 and at least one additional window 18 through which light is detected by a light detecting portion of optical sensor 12.

It is recognized that in sensor 12, and any of the other sensor embodiments described herein, multiple windows may be provided to allow multiple light emitting and/or light detecting portions to be selected in different combinations for performing oxygenation measurements. Different combinations of light emitting and light detecting portions may include using emitting and detecting portions at different distances apart. The distance between the emitting and detecting portions determines, in part, the optical pathway of the sensor and thus the measurement volume. Therefore, selection of different emitting and detecting portions and different emitting-to-detecting spacings allows oxygenation measurements to be performed in different measurement volumes in tissue adjacent to the sensor.

In some embodiments, an optical sensor 20 may be carried by a lead 22 extending from IMD 10. Lead 22 is coupled to circuitry within housing 14 via a connector block 15 including appropriate electrical connections and feedthroughs to allow circuitry within housing 14 to be coupled to sensor 20. A lead-based sensor 20 may be used to deploy sensor 20 at a tissue site remote from the implant site of IMD 10. Lead 22 may be tunneled extravascularly, e.g., subcutaneously or submuscularly, to a desired monitoring site.

In alternative embodiments, a lead 24 carrying a sensor 26 near or at a distal end of the lead 24, may be advanced within the vascular system and remain within a blood vessel 25 for measuring $O_2$Sat and HbT within the blood stream or in tissue adjacent to blood vessel 25. Alternatively, lead 24 may be advanced intravascularly to a desired tissue site then advanced through the vessel wall, for example, by puncturing the vessel wall, for placement at an adjacent tissue site.

Sensors 30a and 30b are shown as wireless sensors including a telemetery module (not shown) enabled for wireless communication with IMD 10 or an external medical device, such as a bedside monitor, home monitor or device programmer. A wireless optical sensor 30a or 30b may be implanted at a desired monitoring site remote from IMD 10 without the surgical constraints imposed by tethering sensor 30A or 30B to IMD 10 using a conductive lead. A wireless sensor 30a or 30b may be implanted for monitoring purposes only, without added therapy delivery capabilities, and may be used alone or in conjunction with another IMD 10.

In other embodiments, an external, wearable optical sensor 40a, 40b, or 40c, collectively referred to as 40, may be provided for ambulatory, chronic or acute monitoring of tissue. Examples of placement of an external optical sensor 40 at different monitoring sites is illustrated in FIG. 1, which may be any external site including the extremities. For example, external optical sensors 40 may include a sensor 40a placed along the thenar muscle (along the palm of the hand just beneath the thumb), a sensor 40b along the upper leg, or a sensor 40c along the lower leg or foot. External sensors 40 may be held in a stable position using an adhesive patch or tape or using a securable band or cuff. External sensors 40 may alternatively be embodied as wired sensors coupled to an external monitor or device programmer.

Figure 2:
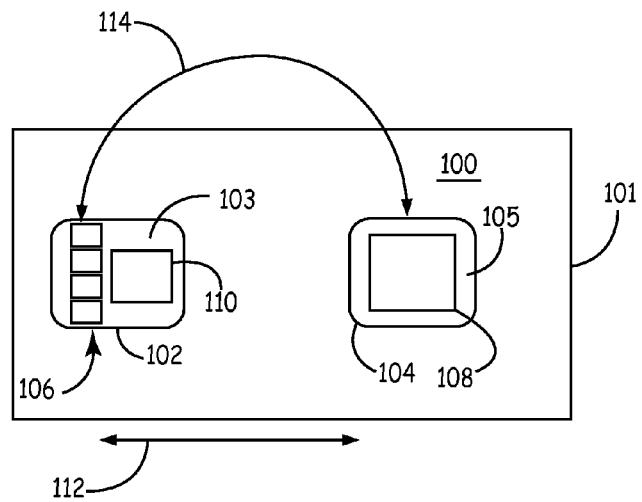
FIG. 2 is a top, schematic view of an optical sensor according to one embodiment.

FIG. 2 is a top, schematic view of an optical sensor according to one embodiment. It is recognized that numerous optical sensor configurations may be used for monitoring tissue oxygenation, and the methods and devices described herein are not limited to a particular optical sensor configuration. In general, any optical sensor that acquires the scattered light intensity measurements required to compute a measurement of $O_2$Sat may be used. Examples of other optical sensors that may be employed for measuring $O_2$Sat and HbT are generally described in U.S. Provisional Patent Application No. 61/185,818 to Kuhn, et al., hereby incorporated herein by reference in its entirety.

In general, any optical sensor that acquires measurements of the attenuation of light scattered by or transmitted through a tissue volume for computing a measurement correlated to tissue oxygenation may be used. In some embodiments, tissue oxygenation measurements may include a non-calibrated index of oxygen saturation determined using a two-wavelength optical sensor, typically emitting and detecting red and infrared light, as generally disclosed in U.S. Patent Application No. 2007/0255148 (Bhunia), hereby incorporated herein by reference in its entirety. In other embodiments, tissue oxygenation measurements may include non-calibrated indices of oxygen saturation and blood volume determined using a two-wavelength (typically red and infrared) optical sensor or a three-wavelength (typically red, isosbestic and infrared) optical sensor as generally described in U.S. Patent Publication No. 2008/0208269 (Cinbis, et al), hereby incorporated herein by reference in its entirety.

The sensor 100 shown in FIG. 2 includes a light emitting portion 102 and a light detecting portion 104. Light emitting portion 102 includes one or more light sources 106 positioned to emit light through a lens 103 sealed in an opening in hermetically-sealed housing 101. Light sources 106 may be embodied as single white light source or multiple light sources emitting light at separate spaced-apart wavelengths. Suitable light sources include, without limitation, optoelectronic devices such as light emitting diodes (LEDs), lasers such as vertical cavity surface emitting lasers (VCSELs), luminescent or phosphorescent and incandescent light sources. In one embodiment, light sources 106 are embodied as LEDs emitting light in the visible, e.g. red, and/or infrared light spectrum.

For example, four LEDs may be included in emitting portion 102 for emitting light at separate wavelengths of 680 nm, 720 nm, 760 nm, and 800 nm. Alternatively, four LEDs provided as light sources 106 may emit light at 660 nm, 720 nm, 760 nm, and 810 nm. In another embodiment, four LEDs are included emitting light at 720 nm, 760 nm, 810 nm, and 850 nm. In yet another embodiment, four LEDs are included that emit light at 720 nm, 760 nm, 810 nm, and 890 nm. Any combination of light sources emitting light at any of the wavelengths mentioned herein may be used. Furthermore, it is recognized that the specified wavelengths are approximate and each light source may emit a narrow band of light wavelengths which is approximately centered on, or at least includes, the specified wavelength. The light sources may be controlled to emit light sequentially or simultaneously.

In the embodiment shown, the light emitting portion 102 further includes a reference light detector 110, which may be embodied, for example, as a photodiode. The light entering an adjacent tissue volume from emitting portion 102 may change over time during chronic use of sensor 100 due, for example, to drift in the photonic output of light source(s) 106 and/or changes in the optical properties of the materials encountered by light emitted by light sources 106 before entering an adjacent tissue volume, e.g. lens 103. Reference light detector 110 provides an output signal for measuring or detecting changes in the intensity of the light emitted by emitting portion 102.

The reference light detector 110 output signal can be used in computing or adjusting $O_2$Sat and HbT measurements. Additionally or alternatively, an output signal from reference light detector 110 can be used as a feedback signal for controlling the drive signals applied to light sources 106 to cause light emission.

In other embodiments, a light detector is not included in the emitting portion 102. The emitted light intensity is assumed to be stable throughout the usable life of the sensor so as not to introduce significant error in attenuation measurements.

The light detecting portion 104 includes a light detector 108 positioned to receive light through a lens 105 mounted in an opening in housing 101. The light detector 108 may be embodied as a photodiode. Other components suitable for use as a light detector include a photoresistor, phototransistor, photovoltaic cell, photomultiplier tube, bolometer, charge-coupled device (CCD) or an LED reverse-biased to function as a photodiode. Light detector 108 receives light scattered by an adjacent tissue volume. The distance 112 between the light sources 106 and the light detector 108 will influence the optical path length 114, shown schematically. Greater spacing (longer distance 112) between the emitting and detecting portions will result in a longer optical path, extending deeper in the adjacent tissue volume, than relatively shorter spacing between light sources 106 and light detector 108.

Figure 3:
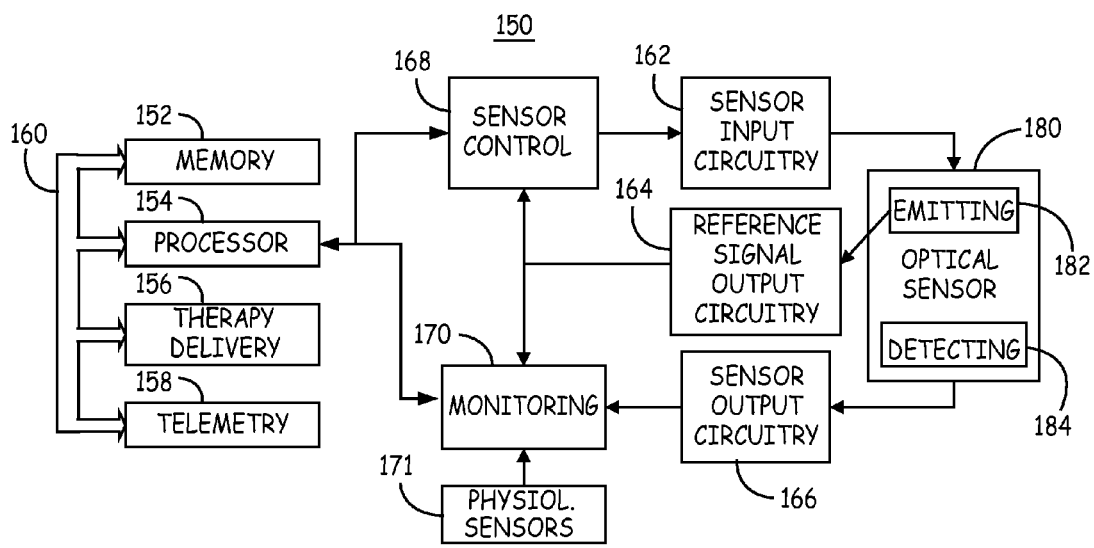
FIG. 3 is a functional block diagram of a medical device including an optical sensor for monitoring tissue oxygenation.

FIG. 3 is a functional block diagram of a medical device 150 including an optical sensor 180 for monitoring $O_2$Sat and HbT. Device 150 and variations thereof may generally correspond to IMD 10, a wireless sensor 40, or an external sensor 30 (all shown in FIG. 1). Device 150 includes an optical sensor 180, which may be incorporated in or on a sealed housing of device 150, carried by a lead extending from device 150, or located in a separate housing. Device 150 further includes sensor input circuitry 162, sensor output circuitry 166, and optionally includes reference signal output circuitry 164 when a reference light detector is included in the optical sensor 180 for measuring the intensity of emitted light.

Optical sensor 180 generally includes a light source for emitting light through a blood perfused tissue (and/or blood) of the patient and a light detector for generating a signal representative of an intensity of light scattered by the blood perfused tissue to the light detector. The light passed through the tissue or bloodstream may be selected to include four or more wavelengths for use in computing a volume-independent measure of $O_2$Sat, from which an absolute, calibrated $O_2$Sat may be derived. Typically, the intensity of scattered light falling in the red part of the visible light spectrum and the infrared (IR) portion of the light spectrum is measured. The light scattered by the blood perfused tissue and received by the light detector is generally correlated to the oxygen available ($O_2$Sat and HbT) to the tissue. Processing of the optical sensor output signal thus allows tissue oxygen availability to be measured for monitoring a patient condition.

Sensor input circuitry 162 is coupled to a light emitting portion 182 of optical sensor 180. Light emitting portion 182 includes one or more light sources for emitting light. Light sources may emit light at discrete, spaced-apart wavelengths or a single white light source may be used. The measurement of scattered light for at least four different wavelengths allows a calibrated absolute $O_2$Sat measurement to be obtained as will be described herein. Sensor input circuitry 162 provides input signals to the optical sensor 180. In particular, sensor input circuitry 162 provides the drive signals applied to the light source(s) included in light emitting portion 182 to cause controlled light emission, e.g. controlled intensity, time duration and frequency.

Sensor input circuitry 162 is controlled by sensor control module 168 which coordinates the beginning time, duration, and frequency of drive signals produced by sensor input circuitry 162. Drive signals may be applied to individual light sources simultaneously to cause "mixed" light emission from all light sources. Control signals may include a period of no light emission for ambient light measurement. In one embodiment, the drive signals are applied sequentially to cause sequential (i.e., non-simultaneous) light emission by individual light sources emitting light at spaced apart wavelengths. In this way, a light detecting portion 184 of sensor 180 will receive scattered light at an individual wavelength at any given time during the operation of sensor 180. It is recognized that referring to an "individual" or "one" wavelength can include a narrow bandwidth of wavelengths approximately centered on, or at least including, the specified individual wavelength emitted by a light source.

The sequential emission of light wavelengths allows multiple, scattered light signals to be sequentially measured for each wavelength. A single $O_2$Sat or HbT measurement will require some minimum interval of time corresponding to the cumulative time durations of each of the separately emitted wavelengths. The time-based sequencing of emitted light may include an interval of no light emission to allow for ambient light measurements and correction of the measured light signals for the presence of ambient light during light emission by the sensor.

In alternative embodiments, the sensor input circuitry 162 is controlled by sensor control module 168 to deliver drive signals simultaneously to each of the light sources at separate, unique frequencies. For example, light sources may be controlled to emit light simultaneously with each wavelength having a signature frequency fluctuation. The detecting portion 184 will receive scattered light at all of the wavelengths corresponding to the light source wavelengths simultaneously with each wavelength modulated to a signature frequency. A light detector signal is then demodulated to obtain the individual wavelength signals.

This frequency multiplexing method of controlling the light emitting portion 182 allows simultaneous light emission and detection such that changes in light attenuation by the tissue due to oxygen and hemoglobin changes in the measurement volume can be measured simultaneously for all of the wavelengths rather than at discrete time intervals. This allows for a more instantaneous measurement of $O_2$Sat and HbT as compared to the sequentially-acquired signals for separate wavelengths in the time-multiplexed method of controlling light emission.

The different wavelengths may be modulated at frequencies that are much greater than the frequency of ambient light changes. Demodulation of the detected light signal will reduce or eliminate effects of ambient light artifact since low frequency components of the detected light signal corresponding to ambient light changes will be substantially removed from the demodulated light detector output signal.

Sensor output circuitry 166 receives the light detector signal from light detecting portion 184 and demodulates, digitizes, or performs other signal conditioning to provide a digital signal to monitoring module 170. Sensor output circuitry 166 may include an analog-to-digital converter and memory for digitizing an analog output signal from detecting portion 184, providing the digitized signal to monitoring module 170, storing measurement results for future retrieval as well as storing calibration coefficients.

Monitoring module 170 uses the optical signal to compute a measurement of $O_2$Sat and a measurement of HbT using the attenuation of the multiple wavelengths measured by detecting portion 184. In some embodiments, a calibrated absolute $O_2$Sat and calibrated HbT are derived from the measurements and provided to a processor 154 (or other control circuitry) for monitoring tissue oxygenation. In particular, the $O_2$Sat and HbT measurements may be used to detect a patient condition associated with a change in the availability of oxygen to the tissue.

Device 150 optionally includes a therapy delivery module 156. The monitored $O_2$Sat and HbT may be used in determining when a therapy is needed and in controlling therapy delivered by therapy delivery module 156. Therapy delivery module 156 may include electrical pulse generation capabilities for delivering cardiac pacing pulses, cardioversion/defibrillation shocks, or nerve stimulation therapies. Therapy delivery module 156 may additionally or alternatively include a fluid delivery pump for delivering a pharmaceutical or biological fluid to the patient, such as cardiac drugs, insulin, or other therapeutic fluids.

Device 150 may include other sensors 171 for sensing physiological signals such as ECG or cardiac EGM signals, blood pressure, patient activity, patient posture, temperature, or the like. Such sensor signals may be used in combination with the monitored $O_2$Sat and HbT for detecting a patient condition. Other physiological sensors may also be used in triggering the acquisition of $O_2$Sat and HbT measurements, adjusting thresholds for detecting tissue hypoxia, and establishing different baseline $O_2$Sat and HbT measurements for different patient conditions (e.g., different activity levels, different patient postures, etc.).

Data acquired by processor 154 relating to $O_2$Sat and HbT may be stored in memory 152 and/or transferred to a medical device programmer, home monitor, computer, or other external or bedside medical device via wireless telemetry module 158 for display and/or review by a clinician. Data relating to $O_2$Sat and HbT may also be transmitted to another implantable or external medical device for use in controlling a device delivered therapy. Processor 154 transmits data to and from memory 152, therapy delivery module 156, and telemetry module 158 via data/address bus 160.

As will be described herein, some embodiments include a reference light detector in the light emitting portion 182 of sensor 180. Reference signal output circuitry 164 may then be included for receiving a light detection signal from the reference light detector and providing a reference output signal to sensor control 168 and/or to monitoring module 170. In one embodiment, the reference signal output circuitry provides an emitted light intensity feedback signal to sensor control 168 in a feedback control loop to maintain emitted light at each wavelength at desired relative intensities. Drive signals applied to a light source in light emitting portion 182 can be automatically adjusted to maintain the emitted light within a desired intensity range for each wavelength measured by the detecting portion 184. In this way, the emitted light spectra is reliably maintained over time promoting the accuracy of $O_2$Sat and HbT measurements computed using stored calibration constants or assuming stable light emission intensity. Accordingly sensor control 168 may include comparators, analog-to-digital converters, and other logic circuitry for determining if a reference emitted light intensity signal is within a target range. If not within the desired range, the drive signal is adjusted by sensor control 168, e.g., in an iterative manner, until the target range is reached.

In an alternative embodiment, the reference emitted light intensity signal provided by circuitry 164 is received by monitoring module 170. Monitoring module 170 may use the emitted light intensity and a detected light intensity to compute light attenuation at each desired wavelength. The attenuation at each wavelength can be used to compute second derivative attenuation spectra as will be described in greater detail below which enables derivation of a volume-independent, absolute measure of $O_2$Sat.

Alternatively, monitoring module 170 uses changes in the emitted light intensity to adjust a computed $O_2$Sat. $O_2$Sat may be computed assuming a stable emitted light intensity. The actual emitted light intensity may be measured and used to adjust a computed $O_2$Sat. For example, an initially measured emitted signal intensity and a currently measured emitted signal intensity can be used to adjust or correct an absolute $O_2$Sat and HbT computed using only the light detector signal from detecting portion 184 and calibration constants.

Figure 4:
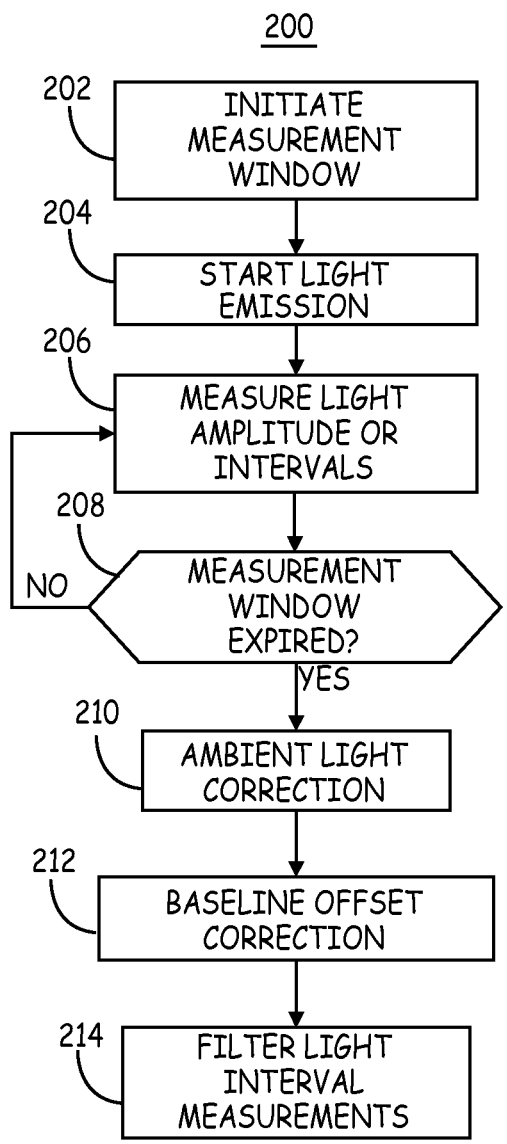
FIG. 4 is a flow chart of a method for operating an optical sensor to obtain light detector output signals during tissue oxygenation monitoring.

FIG. 4 is a flow chart of a method 200 for operating an optical sensor to obtain light detector output signals during tissue oxygenation monitoring. Flow chart 200 and other flow charts presented herein are intended to illustrate the functional operation of the device, and should not be construed as reflective of a specific form of software or hardware necessary to practice the methods described. It is believed that the particular form of software, hardware and/or firmware will be determined primarily by the particular system architecture employed in the device and by the particular detection and therapy delivery methodologies employed by the device. Providing software to accomplish the described functionality in the context of any modern medical device, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

At block 202, a measurement time window is initiated. In various applications, tissue oxygenation monitoring may be continuous, periodic, or triggered in response to detecting physiological events monitored by the medical device, such as arrhythmias, hemodynamic changes, changes in patient activity or posture, or the like. In the example shown in method 200, tissue oxygenation monitoring is performed during a periodic or triggered measurement window. After initiating the measurement window, light emission is started at block 204. Light emission at selected wavelengths may be controlled in a time multiplexed or frequency multiplexed manner or provided as pulsed or continuous white or simultaneously-emitted mixed light.

At block 206, the electrical output signal generated by the light detector is measured. The output signal may be analyzed using an amplitude approach or an integration approach. In the integration approach, an integrator is included in the sensor output circuitry for integrating the light detector signal, for example using a capacitor. The signal may be integrated over fixed time intervals, which may be on the order of approximately 0.10 to 100 ms for example. The magnitude of the integrated signal at the end of the fixed time interval is stored as a sample data point and corresponds to scattered light received by the light detecting portion of the optical sensor during the fixed time interval. Alternatively, the light detector signal may be integrated until a predetermined integrated signal magnitude is reached and the time interval required to reach the predetermined magnitude is stored as a sample data point.

In other embodiments, the amplitude of the light detector signal may be monitored directly by sampling the signal amplitude throughout the measurement window. Such sampling may correspond to sequential time intervals of light source activation times during time multiplexed light source operation. Alternatively the frequency may be selected to be greater than the greatest frequency modulation of a light source in the emitting portion to allow sampling all of frequencies of emitted light in a frequency multiplexed algorithm.

The measurement window may be set to allow time to acquire a desired number of output signal sample points for each of the desired wavelengths. The light detector signal amplitude or integrated signal amplitude or time interval continues to be sampled during the measurement window until it expires as determined at decision step 208. Depending on whether the measurement window is initiated as a periodic monitoring window or a triggered monitoring window, the duration of the measurement window may vary from a few seconds to a few minutes or longer.

After acquiring the desired number of samples, the drive signals controlling the light emitting portion may be turned off. The sampled data points may be stored and processed for computing oxygenation measurements. The sampled data points may be filtered or averaged at block 214 to provide smoothing of signal data or removal of artifact.

At blocks 210 and 212 corrections of sample data may be made to reduce the influence of ambient light and baseline offset. Corrections performed in blocks 210 and 212 may be executed before or after filtering at block 214. Ambient light may be measured directly by measuring the optical signal when the light emitting portion of the optical sensor is not emitting light. The ambient light contribution may then be subtracted from the light signal. Baseline offset (sometimes referred to as the "dark signal" or "dark interval") is caused by current leakage within the optical sensor electronics that occurs in the absence of light. Correction for the baseline offset for a given sensor can be made based on a dark signal or dark interval for that sensor, measured, for example, at the time of device manufacture and qualification testing. If the baseline offset exceeds a desired threshold, offset correction may be included at block 212 to subtract the offset from the incoming signal data. The resulting filtered, corrected sampled signal for each of the wavelengths of interest can be processed as will be further described herein for obtaining a volume-independent measurement of $O_2$Sat and a measurement of HbT for assessing oxygenation of the adjacent tissue volume.

Figure 5:
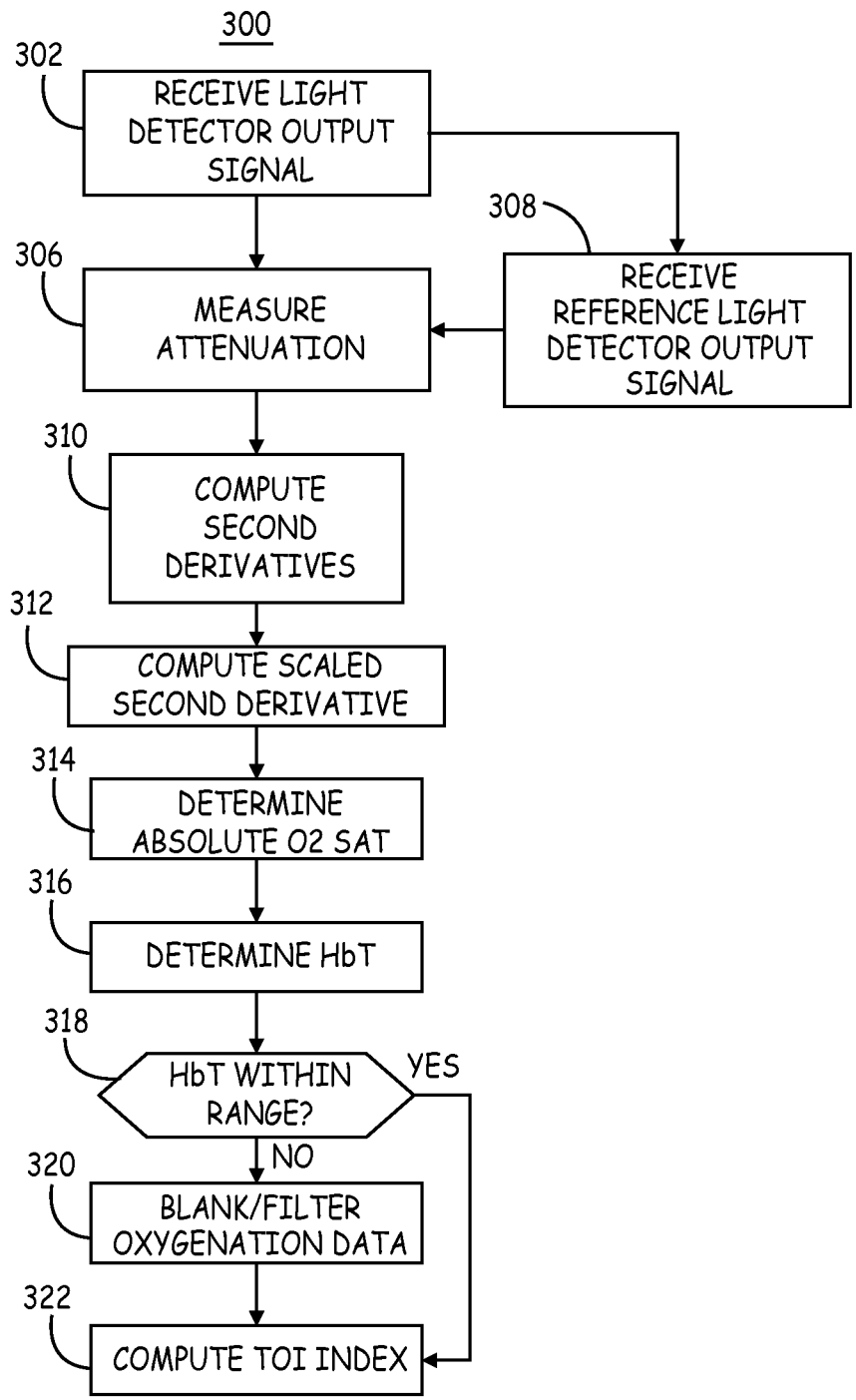
FIG. 5 is a flow chart of a method for operating an optical sensor during tissue oxygenation monitoring.

FIG. 5 is a flow chart of a method 300 for operating an optical sensor during tissue oxygenation monitoring. Method 300 generally corresponds to sensor operation after implantation and calibration, which will be further described in conjunction with FIG. 7. Once the sensor is calibrated and acceptably positioned at a monitoring site, it is enabled for monitoring tissue oxygenation according to a programmed monitoring algorithm. For example, method 300 generally corresponds to operations performed during continuous, periodic or triggered tissue oxygenation monitoring.

At block 302, the optical sensor is controlled to emit light and the light detector output signal is received from the light detecting portion of the sensor. The light detector output signal may be filtered and corrected for ambient light and baseline offset as described above. If a reference light detector is included in the light emitting portion, the reference light detector provides an output signal for measuring the intensity emitted by the sensor at block 308.

At block 306, the attenuation spectrum is measured. In one embodiment, the attenuation of four wavelengths in the red to infrared spectrum is measured. The attenuation of the four different wavelengths may be measured using sequential detection of the different wavelengths by the light detector when a time multiplexed light emission control algorithm is used. Alternatively, measurement of the four different wavelengths may involve demodulation of simultaneously detected light at the four different wavelengths when frequency multiplexed light emission is used. In other embodiments, remitted light from a white light source or simultaneously emitting separate light sources may be filtered to obtain the four different wavelength attenuation signals. Remitted light is the light that is scattered by the adjacent tissue volume and received by the optical sensor. The attenuation of remitted light for a given wavelength ($\lambda$) can be measured as the negative logarithm of the ratio of the emitted light intensity ($i_{in}$) to the remitted light intensity ($i_{out}$):

$$A(\lambda) = -\log(i_{in}/i_{out})_\lambda \qquad [1]$$

wherein $i_{in}$ can be measured using the output signal of a reference light detector in the light emitting portion of the sensor, and $i_{out}$ is measured using the output signal of the light detecting portion for a given wavelength. The term "attenuation" measurement as used herein generally refers to a measure of the attenuation of light due to absorption and scattering by tissue along the optical path of the sensor. The measured attenuation may therefore not be an exact measurement of the actual light absorption by the tissue volume since light reflections and scattering may cause attenuation of the remitted light intensity not attributed to actual light absorption by the tissue.

In alternative embodiments, the emitted intensity $i_{in}$ for each wavelength is measured prior to implantation, e.g., at the time of manufacture, and assumed to be sufficiently stable throughout the usable life of the sensor and not cause significant measurement error. In this case, a reference light detector may be eliminated from the light emitting portion of the sensor and thereby reduce overall size and complexity of the sensor. One method for measuring the emitted intensity prior to implantation uses the light detecting portion to measure the remitted light when the sensor is positioned within a calibrated reflective housing. The construction of the emitting portion is designed to minimize or prevent drift in the emitted light intensity over time. Design considerations include minimizing the distance between the tissue and the photonic surfaces of the light source(s).

The attenuation for four wavelengths is determined to allow the second derivative with respect to wavelength of the attenuation spectra at two intermediate wavelengths to be computed. This determination of second derivatives at two intermediate wavelengths allows for computation of a scaled second derivative as a ratio of the two second derivatives. By properly selecting the intermediate wavelengths, a scaled second derivative is an oxygen-dependent and measurement volume-independent ratio and therefore provides a measure of $O_2$Sat. At block 310, the attenuation measurement for each intermediate wavelength out of the four detected wavelengths is converted to a second derivative (D''), expressed generally as:

$$D''(\lambda_i) = A(\lambda_{i+1}) - 2A(\lambda_i) + A(\lambda_{i-1}) \qquad (2)$$

wherein $A(\lambda_i)$ is the light attenuation, measured according to Equation 1 above, at the wavelength for which the second derivative is being computed, $A(\lambda_{i+1})$ is the attenuation at the next higher wavelength and $A(\lambda_{i-1})$ is the attenuation at the next lower wavelength of the four wavelengths. Equation 2 assumes equal spacings between the four wavelengths. When unequal spacings are used, a different equation for the second derivative with respect to wavelength is required to account for the different wavelength spacings. Reference is made to U.S. Provisional Patent Application No. 61/185,831 to Kuhn et al., incorporated herein by reference in it's entirety.

The second derivative of a selected intermediate wavelength is scaled by the other computed second derivative at block 312. In one embodiment, the attenuation is measured for wavelengths at 680 nm, 720 nm, 760 nm, and 800 nm. The second derivatives of the attenuation spectra are computed at 720 nm and 760 nm and the second derivative at 720 nm is scaled by the second derivative at 760 nm. The scaled second derivative (SD'') of the 720 nm attenuation can be expressed as $$SD'' = D''(720)/D''(760) \qquad (3)$$

This SD''(720) is dependent on oxygen saturation of the hemoglobin present in the measurement volume but independent of the size of the measurement volume, defined by the optical path of the sensor. Thus, SD''(720) is independent of the total hemoglobin present in the measurement volume and independent of the optical path length. The reduced dependence on total hemoglobin and optical path length is expected to reduce the effects of motion artifact on a measurement of $O_2$Sat based on SD''(720). Thus, measuring attenuation for at least four wavelengths allows the second derivatives of two intermediate wavelengths to be computed, allowing computation of a measurement volume-independent, scaled second derivative.

As used herein, a "volume-independent" measure of oxygen saturation refers to a measurement that is substantially independent of the size of the optical sensor path that encompasses a measurement volume within a substantially uniform tissue. In other words, in a uniform, homogenous tissue, a longer optical pathway that encompasses a larger measurement volume and a relatively shorter optical pathway that encompasses a smaller measurement volume within the same uniform tissue will produce substantially equal $O_2$Sat measurements. A volume-dependent measure of oxygen saturation would be dependent on oxygen and the measurement volume and would thus produce two different measurements for two different measurement volumes in the same uniform, homogenous tissue. The second derivative method for computing $O_2$Sat as described herein eliminates scattering effects of a changing measurement volume and provides a volume-independent measurement of $O_2$Sat.

A homogenous tissue is a tissue that includes structures that are relatively small compared to the measurement volume. For example, if measurement volume is related to emitting-to-detecting spacing, a homogenous tissue might be a tissue wherein tissue structures or features have a dimension of approximately 1/10 of the emitting-to-detecting spacing or less. A uniform tissue is a tissue that has uniform oxygenation through the depth of the measurement volume in contrast to an oxygenation gradient. If a tissue is non-uniform or nonhomogeneous, different oxygen saturation measurements will be obtained depending on the optical path of the sensor.

Once the scaled second derivative is obtained, the stored calibration data is used at block 314 to derive the absolute $O_2$Sat. The second derivative for attenuation at 720 nm wavelength (and 760 nm) is dependent on oxygen saturation and total hemoglobin. Thus, at block 316, HbT may be determined knowing the D"(720) (or D"(760)) with respect to wavelength, the derived absolute $O_2$Sat, and the stored calibration data.

Tissue oxygenation, or the availability of oxygen to tissue, as defined herein, is a function of both tissue $O_2$Sat and HbT. Depending on the particular tissue oxygenation monitoring application, the derived $O_2$Sat and HbT may each be used separately in a monitoring algorithm or combined to determine a tissue oxygenation index used to monitor a patient's status and/or detect a physiological condition. At block 322, a tissue oxygenation index may be computed as a function of $O_2$Sat and HbT. For example, a tissue oxygenation index (TOI) may be a weighted combination of the $O_2$Sat and HbT measurements. In one embodiment, a tissue oxygenation index is computed as:

$$TOI = W_1 O_2 Sat + W_2 HbT \quad (4)$$

wherein $W_1$ and $W_2$ are weighting factors selected for a particular application. may be tailored to an individual patient. It is contemplated that non-linear combinations of $O_2$Sat and HbT may also be used.

Thus, a tissue oxygenation index computed using absolute measurements of $O_2$Sat and HbT can be available on a continuous, periodic or on-demand basis. The TOI and/or the individual calibrated values of $O_2$ Sat and HbT may be used for tracking a patient's baseline tissue oxygenation, changes in patient status based on changes in oxygenation, and in detecting physiological events or conditions associated with an alteration in the tissue oxygenation at the monitoring site.

The absolute values of $O_2$Sat, HbT and the TOI computed using the calibrated absolute values of $O_2$Sat and HbT are computed and stored by the medical device. Additionally, differences between each of these oxygenation measures and a baseline or other earlier corresponding measure may be computed and stored as calibrated trended variables. As such, in addition to storing the absolute values, trended values of each of the oxygenation measurements may be stored as changes in the absolute values over time, referred to as $dO_2$ Sat, dHbT or dTOI, which each represent the difference between a current measurement and a previous measurement of the same calibrated measurement.

Alternatively or additionally, non-calibrated values and trends of the oxygenation measurements may be determined and stored. Since sensor calibration can be time consuming and adds to computational burden for computing a calibrated measurement, it may be desirable to compute non-calibrated values and trends of oxygenation measurements without conversion of those measurements to an absolute value. For example, a scaled second derivative of a properly selected wavelength, SD"($\lambda$), is a volume-independent measure of $O_2$Sat and may be determined as an index of $O_2$Sat without conversion to a calibrated measurement. Likewise, D"($\lambda$), which is volume and oxygen dependent, can provide an index of HbT without conversion to a calibrated measurement. Each of these uncalibrated tissue oxygenation measurements may be used individually as baseline indices of tissue oxygenation or combined in a computation of a TOI, such as a weighted linear combination of the uncalibrated measurements similar to Equation (4) above.

The uncalibrated measurements of SD"($\lambda$), D"($\lambda$), and a TOI computed using SD"($\lambda$) and D"($\lambda$) may be determined and stored when the medical device is initially deployed for tissue monitoring for use as baseline measurements and measured for monitoring patient status and for use in detecting physiological events and optionally for controlling device-delivered therapies. Trends in each of the uncalibrated measurements over time, referred to as dSD"($\lambda$), dD"($\lambda$), and dTOI, may also be determined and stored as the difference between a current uncalibrated measurement and a previous corresponding measurement. In summary, various algorithms for monitoring tissue oxygenation may utilize calibrated measurements ($O_2$ Sat and HbT), trends in the calibrated measurements ($dO_2$Sat and dHbt), uncalibrated measurements (SD"($\lambda$) and D"($\lambda$)), trends in the uncalibrated measurements (dSD"($\lambda$) and dD"($\lambda$)) or any combination of the foregoing measurements and trends.

The oxygen saturation measurement derived from a scaled second derivative is a volume-independent measurement and is therefore expected to have reduced susceptibility to motion artifact, which could alter the optical path of the sensor and thus alter the measurement volume. However, some embodiments may utilize the measured HbT, which is dependent on the measurement volume, to filter or blank tissue oxygenation monitoring during periods in which HbT is out of a normal range, which may be due to motion or activity of the patient.

Accordingly, in one embodiment, the measured HbT is compared to an acceptable range, e.g. between approximately 1% and approximately 25%, at block 318. If HbT is out of the acceptable range, tissue motion may be causing erroneous HbT measurements. At block 320, the tissue oxygenation measurement is blanked or otherwise deemed invalid based on the out-of-range HbT measurement. For example, patient activity may result in oscillatory movements that produce a signal that is intermittently in and out of the acceptable range. Intervals in which the HbT measurement is out-of-range may be blanked for determining a tissue oxygenation index. During intervals in which the HbT measurement is in range, the tissue oxygenation index is computed at block 322. When HbT is out of range, the absolute tissue oxygen saturation measurement may also be ignored or still be determined and stored since it is a volume-independent measurement.

Figure 6:
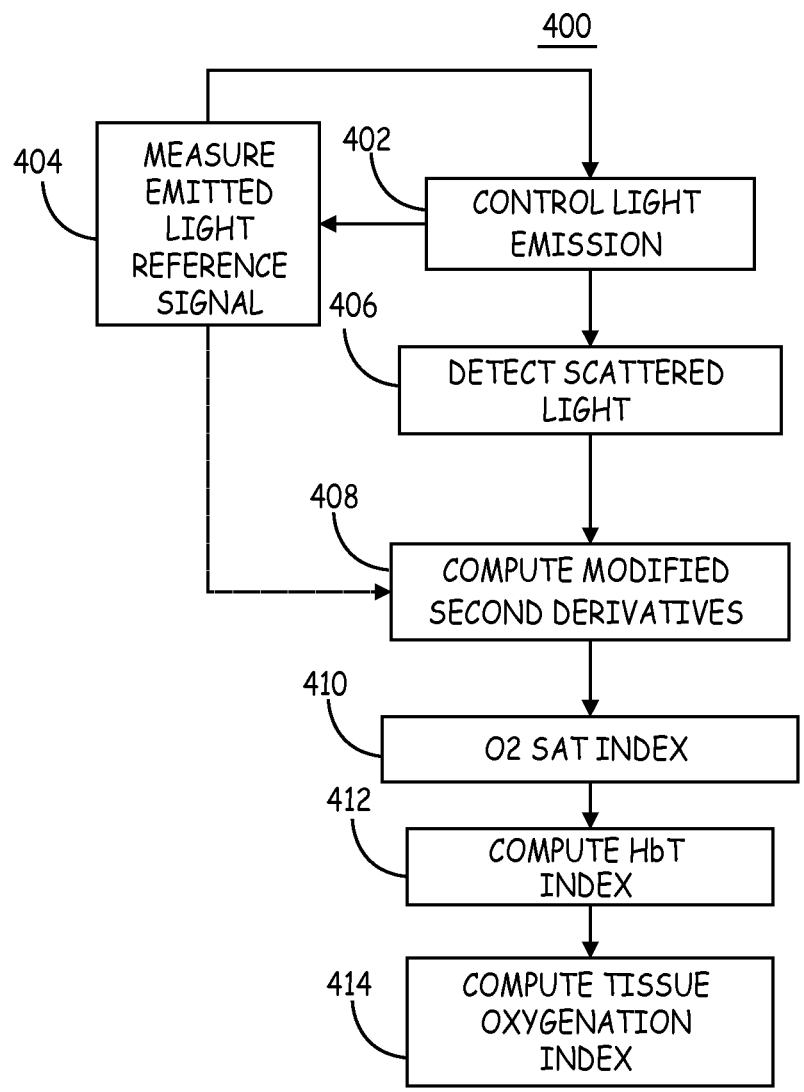
FIG. 6 is a flow chart of an alternative method for using an optical sensor for monitoring tissue oxygenation.

FIG. 6 is a flow chart of an alternative method 400 for using an optical sensor capable of measuring absolute tissue oxygen saturation for monitoring tissue oxygenation. At block 402, control signals are applied to drive circuitry to control the emission of light from the light emitting portion of the optical sensor.

A reference light detector is included in the light emitting portion of the sensor to provide a reference signal measuring the emitted light. The intensity of the emitted light may be controlled using a reference feedback signal as indicated by block 404. In method 400, the emitted light intensity is measured using the reference light detector for controlling light emission such that the emitted intensity ($i_{in}$) at each of the wavelengths used for attenuation measurements is maintained within a specified range.

An emitted light reference signal measured at block 404 using the reference light detector output signal is provided as feedback to the control module controlling light emission at block 402. Drive signals applied to the light emitting portion may be adjusted in response to the emitted light reference signal to maintain the emitted light intensity within a target range for each wavelength selected for attenuation measurements.

When the emitted light is controlled to be maintained within a specified range, the emitted light intensity in the attenuation Equation (1) above becomes a constant. Manipulation of the second derivative Equation (2) above results in a modified second derivative equation:

$$D''(\lambda_i)_{modified} = C_i - \log(i_{out})_{\lambda,i+1} + 2\log(i_{out})_{\lambda,i} - \log(i_{out})_{\lambda,i-1} \quad (5)$$

which may be rewritten as:

$$D''(\lambda_i)_{modified} = C_i + \log\{(i_{out})_{\lambda,i}^2/((i_{out})_{\lambda,i+1})(i_{out})_{\lambda,i-1})\} \quad (6)$$

The term $C_i$ for a given wavelength $\lambda_i$ becomes a calibration constant. Thus, a modified scaled second derivative may be computed using only the detecting portion output signal and the calibration constants $C_i$ determined for each of the measured wavelengths. In the case where there is no reference measurement for emitted light intensities at each wavelength, but the drive signal to the light sources is controllable, the constants $C_i$ are predetermined functions of the drive signal. Note that the above Equation 6 is written for equal wavelength spacing and will include more terms for non-equal wavelength spacing.

The scattered light is detected by the optical sensor at block 406 and used to compute the modified second derivatives at block 408 at two (or more) intermediate wavelengths. The modified second derivatives need only be computed for two intermediate wavelengths being used to compute $O_2Sat$ and HbT.

A simplified scaled second derivative may be used as an estimate of tissue oxygen saturation in which the $C_i$ constants are ignored in the above equations. A simplified scaled second derivative may take the form of:

$$SD'' = \frac{-\log(i_{out})_{\lambda i+1} + 2\log(i_{out})_{\lambda i} - \log(i_{out})_{\lambda i-1}}{-\log(i_{out})_{\lambda i+2} + 2\log(i_{out})_{\lambda i+1} - \log(i_{out})_{\lambda i}} \quad (7)$$

This simplified scaled second derivative may be useful for measuring an uncalibrated, index of $O_2Sat$ at block 410. A corresponding uncalibrated index of HbT may be computed at block 412 using the simplified second derivative computed using Equation 6. The $O_2Sat$ and HbT indices may be used individually or combined in a TOI computed as a function of both at block 414.

In addition or alternatively to using the emitted light reference signal as feedback to control light emission, the emitted light reference signal may be used by the monitoring module to adjust the computed modified second derivatives at block 408. Shifts in the intensity of the emitted light may be accounted for by introducing a correction term in the equation used to compute the modified second derivative. Accordingly, an adjusted modified second derivative for a selected intermediate wavelength used to compute absolute oxygen saturation might be computed using:

$$D''(\lambda_i)_{modified} = C_i - \log(i_{out} + CT)_{\lambda,i+1} + 2\log(i_{out} + CT)_{\lambda,i} - \log(i_{out} + CT)_{\lambda,i-1} \quad (8)$$

wherein CT is a correction term, which may be a positive or negative value, determined for each wavelength using the emitted light reference signal and is used to adjust the remitted light intensities $i_{out}$ for each wavelength.

In the methods described herein for monitoring tissue oxygenation, determining optical sensor status, detecting or predicting tissue hypoxia and controlling device therapies, the modified second derivative computations may be substituted for second derivative computations used in deriving volume-independent indices of $O_2Sat$ and indices of HbT.

Figure 7:
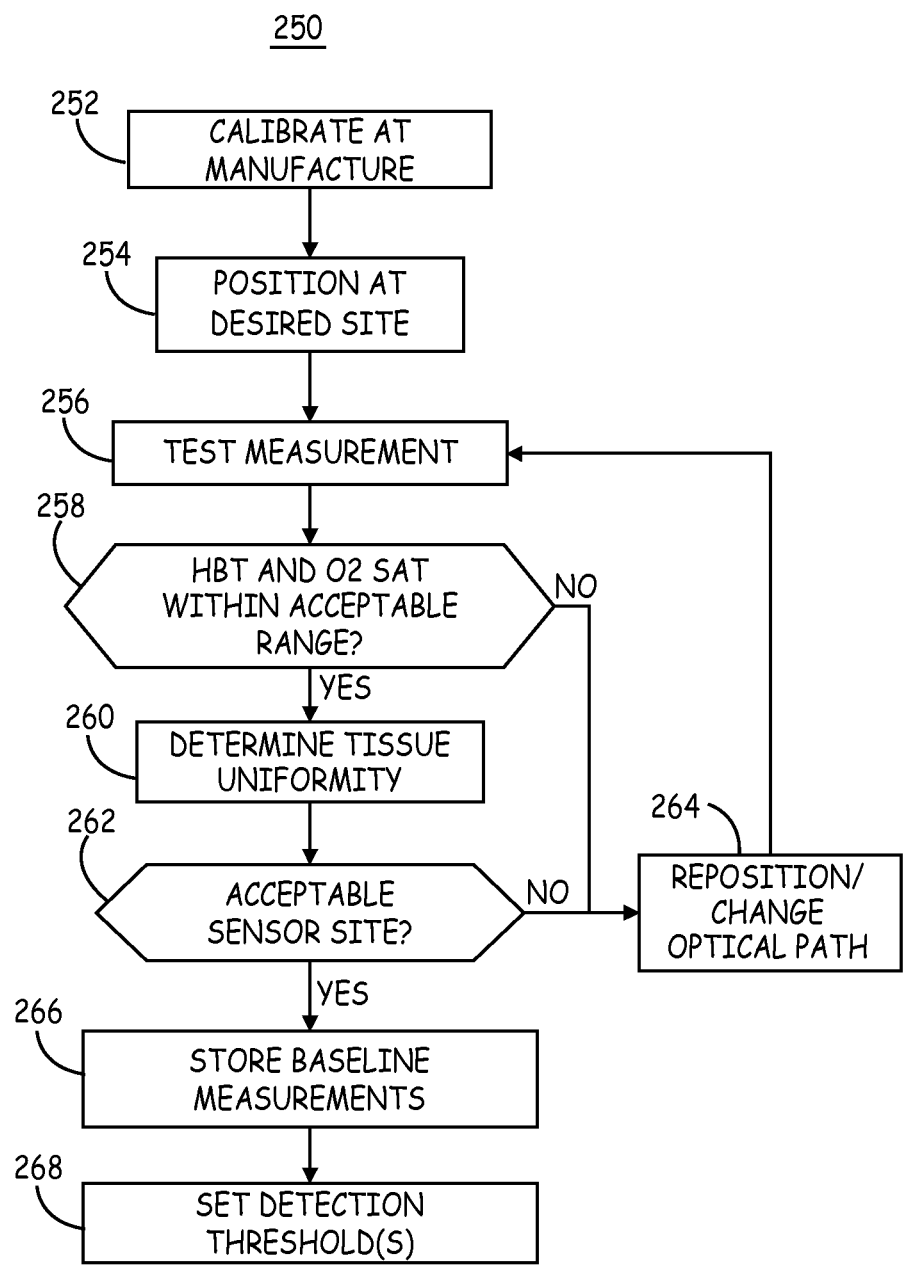
FIG. 7 is a flow chart of a method for using a medical device including an optical sensor for monitoring tissue oxygenation.

FIG. 7 is a flow chart of a method 250 for using a medical device including an optical sensor for monitoring tissue oxygenation. At block 252 of method 250, the optical sensor is calibrated using control samples, for example in an in vitro blood circuit, having known oxygen saturation and total hemoglobin concentration. The calibration method may be used to generate a look-up table. A look-up table of values relating measurements computed from the light detector output signal and the known $O_2Sat$ and HbT may be stored in the device memory. The look-up table can then be used to derive absolute $O_2Sat$ and Hbt values from an optical sensor measurement as will be further described below.

Alternatively, calibration methods may include curve-fitting methods to solve for coefficients defining best-fit curves to the calibration data. In one embodiment, the absolute tissue oxygen saturation is defined by:

$$O_2sat = Ae^{B(SD''(\lambda_i))} + C \quad (9)$$

wherein SD" is a scaled second derivative of the attenuation spectra at a selected intermediate wavelength ($\lambda_i$) emitted and detected by the optical sensor. As described above, a scaled second derivative of the attenuation spectra at a selected wavelength is determined by the monitoring module using the light detector signal. The scaled second derivative is the ratio of the second derivative with respect to wavelength of the attenuation spectra at a selected wavelength $\lambda_i$ to the second derivative of the attenuation spectra at another selected wavelength used for scaling. By properly selecting the wavelength $\lambda$ and the other wavelength used for scaling, the scaled second derivative is an oxygen-dependent and volume-independent ratio. The coefficients A, B and C are determined through best-fit analysis of measurements of the scaled second derivative for calibration samples having known oxygen saturation.

The total tissue hemoglobin volume fraction can be defined by the equation:

$$HbT = [M(100 - O_2Sat)^N + L]*[(D''(\lambda i)/SF] \quad (10)$$

wherein M, N, and L are coefficients determined during calibration and $D''(\lambda i)$ is the second derivative of the attenuation spectra with respect to wavelength at the selected intermediate wavelength $\lambda_i$. $D''(\lambda)$ is measured for samples containing known total hemoglobin volume fraction and known oxygen saturation. The calibration coefficients M, N and L may then be computed for a best-fit of the measured second derivative values and known $O_2Sat$ and HbT. Alternatively, the measured second derivative values and known $O_2Sat$ and HbT may be used to generate a look-up table for converting the measured second derivative values to HbT.

SF is a spacing factor which may be used to adjust for an emitting-to-detecting portion spacing that may be different during tissue measurements than that used during calibration. Since the HbT measurement is dependent on both $O_2Sat$ and the measurement volume, and measurement volume is dependent on the optical path of the sensor, defined at least in part by the spacing between the emitting and detecting portions, the HbT measurement needs to be corrected for changes in emitting-to-detecting portion spacing. For example, the sensor may be calibrated using a nominal emitting-to-detecting portion spacing, however when multiple emitting and/or detecting portions are selectable in a sensor or combination of sensors, the spacing may be different during monitoring than that used during calibration. As such, a spacing factor corresponding to selectable emitting-to-detecting portion spacings may be stored and used to correct the HbT measurement when a different spacing is used during monitoring than during calibration.

At block 254, the sensor is positioned in or on a patient at a desired internal or external monitoring site. A test measurement is performed at block 256. The absolute $O_2$Sat and HbT are determined from the sensor output signal using the stored calibration data. The measured values are compared to an acceptable measurement range at block 258. This comparison may be performed manually or automatically using a programmed range stored in the medical device memory. An acceptable measurement range generally corresponds to an expected physiological range for tissue $O_2$Sat and HbT. For example, an acceptable range for tissue $O_2$Sat might be defined to be between approximately 80% and 90%. An acceptable range for HbT might be defined to be between approximately 1% and 25%. These ranges may vary depending on the type of tissue adjacent to the sensor, the heterogeneity of the tissue, the blood oxygenation state of the patient and other factors. The acceptable measurement range may be defined nominally, determined clinically, or tailored to a given patient.

If the tissue oxygen saturation exceeds a predefined expected range, for example greater than approximately 90%, the sensor may be in a position that results in arterial blood strongly contributing to the tissue oxygen saturation measurement. If the monitoring application is concerned with measuring tissue oxygenation, e.g. in skeletal muscle, rather than arterial oxygen saturation, the sensor may be repositioned at block 264 or a different emitting-to-detecting pair may be selected resulting in a different optical path through the tissue.

Likewise, if the oxygen saturation is too low, for example less than approximately 80%, the sensor may be in a position that results in venous blood strongly contributing to the oxygen saturation measurement. If the absolute oxygen saturation falls below an expected physiological range for the particular sensing application, the sensor may be repositioned at block 264. Alternatively, a different emitting-to-detecting pair may be selected resulting in a different optical path through the tissue.

If the total hemoglobin is less than a predetermined range, for example less than approximately 1%, the sensor may be improperly positioned against the tissue (poor tissue contact) or in a position over a non-tissue medium or low or non-perfused tissue. For example, if the sensor is positioned over fat, scar tissue, clear body fluids, or other implanted medical device components, the total tissue hemoglobin concentration may be below a normal physiological range for blood-perfused tissue. A total tissue hemoglobin of greater than an acceptable physiological range, for example greater than approximately 25%, may indicate blood pooling in the measurement volume beneath the sensor or other sensor measurement error. If the HbT test measurement is outside a predefined acceptable range, the sensor may be repositioned at block 264 or a different emitting and detecting pair selected to change the optical pathway.

Once the $O_2$Sat and HbT measurements are confirmed to be in an acceptable physiological range for the tissue being monitored, at block 258, a tissue uniformity index may be determined at block 260. A tissue uniformity index is determined by utilizing at least two different emitting-to-detecting portion spacings. Accordingly at least two different combinations of light sources and light detectors at two different spacings must be available, on the same or different optical sensors, positioned adjacent a target tissue volume.

When at least two different spacings are available, the absolute tissue oxygen saturation is measured using the two different spacings and compared. A tissue uniformity index may be computed based on the difference between two or more measurements made using different emitting-to-detecting portion spacing. Each measurement would each involve different measurement volumes defined by different optical pathways extending through the tissue. For example, a relatively greater emitting-to-detecting portion spacing would result in greater depth of the optical pathway and thus deeper measurement volume.

If the difference between two measurements is small, the tissue is relatively homogenous and uniform through the depth of the larger measurement volume. If the difference between two measurements is large, the tissue is more heterogeneous. A threshold for detecting uniform/homogenous versus non-uniform/heterogeneous tissue volumes may be selected according to a particular application. Detection of heterogeneous tissue may warrant repositioning of the sensor. A tissue uniformity index may indicate the most appropriate emitter-to-detector spacing for measuring within a desired tissue volume and therefore guide selection of light sources and light detectors when multiple combinations are available.

In summary, the initial $O_2$Sat, HbT, and tissue uniformity measurements can be used individually or in combination to decide if the sensor position is acceptable at block 262. If not the sensor may be repositioned at block 264. Instead of repositioning the sensor when unacceptable tissue uniformity or HbT or $O_2$Sat measurements are obtained, a different optical path may be selected by selecting a different combination of light source(s) and light detector when available. For example, multiple light sources and light detectors may be available in one or more sensors to allow selection of different optical paths.

If the sensor position is acceptable, the sensor may be stably fixed at the desired site. In some monitoring applications, chronic fixation of the sensor may not be required, e.g. if acute measurements are performed at one or more locations. Stable positioning is desired during oxygenation measurements. Baseline $O_2$Sat and HbT measurements may be acquired and stored at block 266 according to the needs of the particular sensing application. Baseline measurements may be acquired for comparison to future measurements, for use in learning algorithms performed during clinical interventions or during naturally occurring physiological events for use in setting thresholds for detecting tissue hypoxia and potentially discriminating between different physiological conditions, or for initiating continuous monitoring of the tissue $O_2$Sat and HbT, i.e. tissue oxygenation, for monitoring patient status.

At block 268 preliminary detection thresholds may be set for detecting physiological events corresponding to tissue oxygenation. For example, thresholds may be set for detecting or predicting tissue hypoxia, which may in turn be used as a detection or warning that a corresponding disease state may be worsening, such as heart failure, diabetes, hypertension, anemia, sleep apnea or other breathing disorders, or the like. A detection threshold may be set based on a percentage change or other defined interval from the baseline measurements.

When HbT and/or $O_2$Sat measurements are out of an acceptable range and a different emitting-to-detecting portion spacing is not available or repositioning at block 264 is not possible (or not performed) baseline measurements may still be stored at block 266 and used for setting patient-specific thresholds at block 268. Patient-specific thresholds of HbT and $O_2$Sat, or a tissue oxygenation index computed from the HbT and $O_2$Sat measurements, may be defined and stored for use in detecting physiological events.

For example, if the $O_2$ Sat measurement is low, e.g. <80%, the sensor may be located near a vein and the contribution of the venous blood in the optical path may be causing the lower measurement. In this case, changes in $O_2$Sat or HbT measurements during tissue hypoxia may be reduced compared to a measurement that is obtained over a capillary bed in the tissue. Likewise if a high arterial blood contribution is present in the measurement due to the sensor being located over an artery, the baseline $O_2$Sat will be higher than when positioned over a capillary bed. A change in $O_2$Sat during tissue hypoxia may again be lower than when the sensor is over a capillary bed. As such, thresholds relating to absolute values of $O_2$Sat and HbT and/or thresholds relating to trends in $O_2$Sat and HbT that are used for detecting physiological events may be adjusted according to baseline measurements. For example, a threshold change in $O_2$Sat for detecting a hypoxic condition may be lowered when a baseline $O_2$Sat measurement is lower (higher venous contribution) or higher (higher arterial contribution) than an expected baseline measurement corresponding to a position over a capillary bed.

Figure 8:
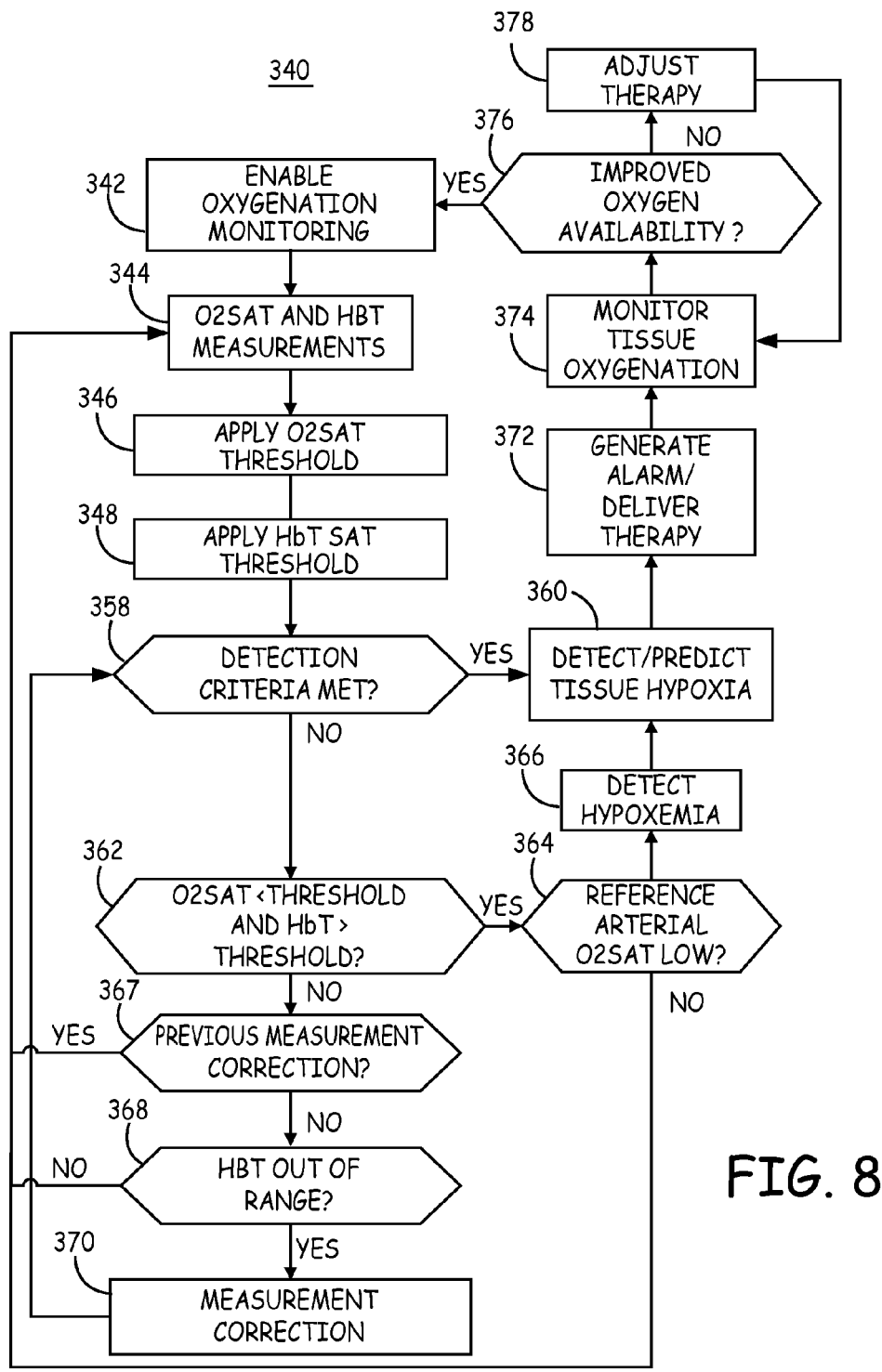
FIG. 8 is a flow chart of a method for monitoring tissue oxygenation for detecting hypoxia.

FIG. 8 is a flow chart of a method 340 for monitoring tissue oxygenation. At block 342, tissue oxygenation monitoring is enabled. Oxygenation monitoring may be enabled at the time of device implantation based on acceptable sensor positioning and baseline measurements.

Tissue oxygenation measurements (i.e. $O_2$Sat and HbT) may be performed on a periodic basis for assessing patient status and sensor function, updating baseline measurements, adjusting detection thresholds, or monitoring for physiological events. Additionally, tissue oxygenation measurements may be performed on a triggered basis in response to a user command, detection of a physiological event based on other sensor signals, or at the onset, during or end of a delivered therapy.

Periodic measurements may be obtained at any desired time interval, for example every few seconds, every minute, hourly, daily weekly, or any other frequency as needed for a particular monitoring application. The frequency of periodic measurements may be adjusted automatically or manually if measurements are desired on a more or less frequent basis. For example, if a change greater than a predetermined percentage or predefined range is detected since a previous measurement, the frequency of periodic measurements may be increased to allow closer monitoring of patient status or early detection of a physiological event.

If it is time for performing periodic or triggered measurements, the optical sensor is operated under the control of a control module to emit and detect light to perform oxygenation measurements at block 344. Performing tissue oxygenation measurements involves computing the uncalibrated $SD''(\lambda)$ and $D''(\lambda)$ values in one embodiment. These values may be stored as indices of $O_2$Sat and HbT or converted to calibrated absolute $O_2$Sat and HbT measurements using stored calibration data when available. A TOI may then be computed using the uncalibrated $SD''(\lambda)$ and $D''(\lambda)$ values and/or the calibrated $O_2$Sat and HbT.

The tissue oxygenation measurements are stored to provide data for evaluating trends in oxygenation measurements or for updating baselines or detection thresholds. The oxygenation measurements may be used to determine and store a status of the optical sensor. If either of the $O_2$Sat or HbT measurements (or $SD''(\lambda)$ and $D''(\lambda)$) are out of the acceptable measurement range, the sensor status may be indicated as unreliable. Tissue oxygenation measurements may be temporarily or permanently disabled based on out of range measurements. If alternative light sources and/or light detectors are available, a different sensor configuration may be selected to obtain measurements within an acceptable measurement range.

Tissue hypoxia detection thresholds may be applied individually to the $O_2$Sat and HbT measurements at blocks 346 and 348 respectfully. Additionally or alternatively, a threshold may be applied to a TOI computed using both $O_2$Sat and HbT measurements. If detection criteria are met at block 358, tissue hypoxia is detected at block 360. Detection criteria may include threshold criteria applied to $O_2$Sat and HbT measurements (which may be obtained at a single time point or include time averaged or median measurements), threshold criteria applied to a TOI, or thresholds applied to trends in any of these measurements. Since tissue oxygen partial pressure is not being measured directly, the $O_2$Sat and HbT measurements relate to the oxygen available to the tissue and thus a detection of tissue hypoxia may be considered a prediction that the tissue is hypoxic or becoming hypoxic based on the oxygen available to the tissue.

Trend analysis may performed using $O_2$Sat (e.g., $dO_{2Sat}=O_2 \text{ Sat}_i - O_2 \text{ Sat}_{baseline}$), HbT ($dHbT=HbT_i-HbT_{baseline}$) and/or a TOI ($dTOI=TOI_i-TOI_{baseline}$) computed as a function of both $O_2$ Sat and Hbt. The trends may be computed using a previous measurement, a running average or other previously identified baseline measurement. The trend analysis may alternatively be performed using the uncalibrated indices of $O_2$ Sat, HbT and/or a TOI computed therefrom, i.e. $dSD''(\lambda)$ and $dD''(\lambda)$ and/or dTOI wherein the TOI is computed as a function of both $SD''(\lambda)$ and $D''(\lambda)$. A threshold applied to the trends may be defined for each of the oxygenation measurements independently or a single threshold may be defined for the TOI. For example, a detection threshold applied to $dO_2$Sat might be defined as a 5% decrease from a baseline $O_2$Sat. If the baseline tissue $O_2$Sat is 85%, 5% of the baseline $O_2$Sat is 4.25%. As such, if the baseline $O_2$Sat is 85% and falls to 80%, the $dO_2$Sat of 5% is greater than the detection threshold of 4.25% resulting in the $dO_2$Sat detection criteria being met. Other detection thresholds may be similarly applied to the trended HbT and/or TOI measurements.

The detection criteria applied at block 358 may include application of a threshold to one or more oxygenation measurements and/or trends. If the threshold criteria defined for detecting tissue hypoxia are not met at block 358, an optional evaluation of $O_2$Sat and HbT individually may be analyzed to determine if tissue hypoxia is present in spite of adequate blood flow to the tissue volume. If the $O_2$Sat measurement is less than a hypoxia detection threshold, but the HbT measurement exceeds a hypoxia detection threshold, as determined at block 362, tissue hypoxia may be present due to inadequate oxygenation of the blood, i.e. hypoxemia.

In some embodiments, another optical sensor (or a different optical pathway on the same sensor but using different light source and light detector) may be available having an optical pathway encompassing a volume of arterial blood. Alternatively, local tissue heating may be applied to cause vasodilation and obtain an estimate of arterial oxygen saturation. A reference arterial $O_2$Sat (and HbT) measurement may be made to determine the oxygenation status of arterial blood at block 364. If the absolute arterial blood $O_2$Sat is determined to be low, e.g. less than approximately 90%, hypoxemia may be detected at block 366. Tissue hypoxia is confirmed at block 360 in response to the low tissue $O_2$Sat measurement corroborated by a low arterial $O_2$Sat measurement at block 360. Otherwise, if a reference arterial $O_2$Sat is not low (block 364), the tissue hypoxia is not confirmed and the process may return to block 344 to continue monitoring tissue oxygenation.

In some embodiments, detection thresholds may be defined based on a Principal Component Analysis (PCA) of the tissue oxygenation measurements. Principal component analysis involves plotting the $O_2$Sat and HbT measurements (or uncalibrated indices thereof) in a two-dimensional space (or an n-dimensional space when additional physiological variables are being used in combination with the oxygenation measurements). A vector identifying a first principal component of variation of the plotted measurements is computed. The first principal component of variation of the measurements may be identified for different types of physiological events and used as a template for detecting a given event when the first principal component of the variation of the oxygenation measurements approaches a stored first principal component template for the given event.

Additionally or alternatively, a vector identifying a first principal component of variation of the plotted measurements during various confounding situations, such as during motion or known patient activities or postures, may be determined for use in artifact removal. In this case, a principal component that is normal (orthogonal) to the first principal component of the plotted measurements in the presence of artifact can be used to remove the effect of the artifact from the measurement variation. Principal component analysis methods generally described in U.S. Pat. Appl. No. 61/144,943 (Deno, et al.), incorporated herein by reference in its entirety, may be adapted for use with the tissue oxygenation measurements described herein. For example, an n-dimensional measurement undergoing principal component analysis may include $O_2Sat$ and HbT or the uncalibrated values of $SD''(\lambda)$ and $D''(\lambda)$ as two of the n dimensions. Alternatively, a TOI computed using a combination of $O_2Sat$ and HbT or $SD''(\lambda)$ and $D''(\lambda)$ may be included as one of the n-dimensions combined with other physiological variables measured using other sensor signals such as blood pressure, heart rate, temperature, etc.

At block 368, the HbT measurement may be monitored to detect an out of range measurement. Sample data points corresponding to an out-of-range HbT may be ignored. Alternatively, HbT values may be used to rank the quality of oxygenation measurements in a measurement correction operation at block 370. For example, if a weighted combination of variables is being used to detect tissue hypoxia or an associated physiological event, less weighting may be applied to HbT (and optionally $O_2Sat$) when HbT measurement(s) are out of an acceptable range. HbT may be ignored or assigned a low weighting based on the range in which the HbT measurement falls. $O_2Sat$ may also be ignored or be used alone in determining a tissue oxygenation status.

After a measurement correction operation is performed at block 370, the detection criteria may be applied again at block 358. If the detection criteria at block 358 and the individual assessment of $O_2Sat$ and HbT at block 362 still do not result in prediction/detection of tissue hypoxia, the method will return to block 344 to continue monitoring. Once measurement correction is performed at block 370, it need not be repeated until new HbT measurements are available. As such, after the individual assessment of $O_2Sat$ and HbT at block 362, a determination may be made at block 367 whether measurement correction has already taken place in response to HbT out of range measurements. If so, the method returns to block 344. If not, the correction is performed one time at block 370.

If HbT is significantly out of range for a large number of sample points, detection of physiological events based on oxygenation measurements may be disabled. A predetermined number of minimum sample points falling within an acceptable measurement range during a monitoring window may be required to rely on a tissue oxygenation-based detection algorithm outcome.

In other embodiments, the amplitude of one light attenuation signal, such as an isosbestic wavelength at approximately 810 nm, may be monitored to determine if the sensor operation is reliable. If the detected signal at a selected wavelength is below a predetermined threshold, than the signal strength is too low to obtain reliable oxygenation measurements. If the detected signal at a selected wavelength is too high, light shunting or reflections may be causing an inaccurately high light signal. Such light signal monitoring may be performed before computing oxygenation measurements with an indication that reliable optical sensing is unavailable.

In response to detecting tissue hypoxia, a patient or physician alarm may be generated at block 372. Methods for generating an alarm include broadcasting an audible sound or delivering electrical stimulation perceptible to the patient, or transmitting a message to a home monitor, computer or other communication networked device.

Additionally or alternatively, a device delivered therapy may be initiated or adjusted at block 372. Device-delivered therapies may include delivering electrical stimulation to the heart, delivering electrical stimulation to a nerve, or delivering a therapeutic fluid into a body tissue or the blood stream. In some cases, adjustment to a device-delivered therapy at block 372 may include terminating the therapy in response to detecting or predicting tissue hypoxia if the tissue hypoxia is suspected to be a side-effect of the therapy.

Tissue oxygenation monitoring may continue at block 374 continuously or periodically in response to changing, initiating, or terminating a therapy. Periodic measurements may be increased in frequency as compared to periodic measurements performed at block 344. If trends in oxygenation measurements show an improvement, as determined at block 376, method 340 may maintain the current therapy delivery (or terminate the therapy delivery if the desired therapeutic response has been reached). Tissue oxygenation monitoring may continue at block 374 or method 340 may return to block 342 as shown to wait for the next scheduled periodic monitoring event.

If oxygenation measurements have not improved at block 376, further adjustments to the therapy may be made at block 378 with continued monitoring at block 374. In this way, tissue oxygenation measurements may be used to provide feedback in the control of a device-delivered therapy. Such feedback control may be used when the therapy is initiated in response to detecting or predicting tissue hypoxia as shown in FIG. 8 or whenever a therapy is being delivered or available.

Improvements in oxygenation measurements at block 376 may be detected through threshold comparisons or analysis of trended measurements as described previously. Evaluation of improvements in oxygenation measurements, i.e. increases in $O_2Sat$ and HbT, may be based on comparisons to the measurements that initially caused the hypoxia prediction/detection at block 360. In other words, the oxygenation measurements meeting detection criteria at block 358 may be stored as episode onset measurements for computing measurement trends with later measurements made during therapy delivery. Alternatively, improvement may be evaluated as an increasing trend toward a previously stored baseline measurement associated with normal tissue oxygenation.

As described previously, tissue oxygenation measurements may include a non-calibrated index of oxygen saturation determined using a two-wavelength or three-wavelength optical. Accordingly, in method 340, indices of tissue oxygen saturation and/or a blood volume index derived from optical sensors measuring two or more wavelengths may be substituted for the specified $O_2Sat$ and HbT measurements obtained using a 4- or more wavelength system and second derivative attenuation measurement methods.

While the flow chart of FIG. 8 provides a general method 340 for detecting tissue hypoxia, the specific monitoring application will determine which measurements are monitored and how threshold criteria are defined. FIGS. 9 through 13 illustrate numerous examples of different tissue oxygenation monitoring devices that may be used for various monitoring applications. For example, method 340 may be adapted for use with any of the sensing devices shown in FIGS. 1 and 9-13 for monitoring tissue oxygenation for determining the status of a variety of pathological conditions.

Figure 9:
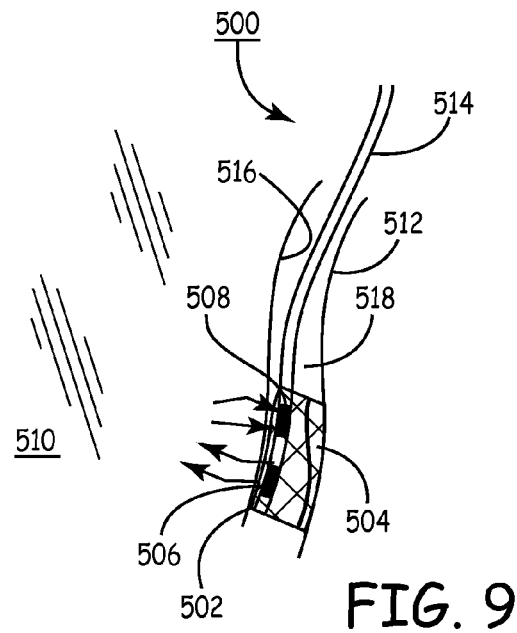
FIG. 9 is a schematic view of an implantable optical sensing device.

In FIG. 9, an implantable optical sensing device 500 includes an elongated lead body 514, an optical sensor 502, and a stent 504 positioned at the distal end of the lead body 514. Optical sensor 502 includes one or more light emitting portions 506 and one or more light detecting portions 508. Lead 514 carries conductors for delivering control signals to the light emitting portion 506 and carrying sensor output signals from light detecting portion 508 to an associated implantable medical device, such as IMD 10 shown in FIG. 1.

Sensor 502 is mounted along an inner or outer radial surface of a stent 504 so as to direct the lenses of the emitting and detecting portions 506 and 508 radially outward, toward the vessel inner wall 516. If placed on an inner surface of stent 504, stent 504 may include open windows or a material that is optically transparent to the wavelengths of interest aligned with the sensor emitting and detecting portions. Stent 504 may be an expandable stent that is deployed to maintain the position of sensor 502 adjacent a desired tissue volume. Stent 504 holds the sensor emitting and detecting portions 506 and 508 in close proximity or directly against (in direct contact with) the inner wall 516 of a blood vessel 512. Stent 504 also maintains the longitudinal position of sensor 502 with respect to a longitudinal axis of the blood vessel 512.

In alternative embodiments, other mechanisms may be employed to maintain the axial position of the sensor 502 and to hold the sensor 502 directly against an inner vessel wall 516. Other mechanisms may include an inflatable balloon, tines, or preformed curves formed in lead body 514. Such mechanisms may protrude in a direction opposite the direction of sensor orientation to thereby urge the sensor 502 toward and against inner wall 516 such that sensor 502 is positioned to obtain light signals from a measurement volume extending into tissue 510 adjacent to vessel 512. For example, a balloon or extending tines may be mounted along the backside (opposite the windows of emitting and detecting portions 504 and 506) of sensor 502. When inflated or extended, the balloon or tines would press against the inner vessel wall opposite the sensor 502 thus pushing the sensor 502 against inner wall 516. Typically blood vessel 512 will be a vein however sensing device 500 may also be advanced into an artery.

During sensor operation, light is emitted and scattered by the blood vessel wall and adjacent tissue 510. The spacing between emitting portion 506 and detecting portion 508 is selected to provide a desired depth of the optical pathway into the adjacent tissue volume 510 such that a majority of the optical pathway encompasses tissue volume 510. In this way, oxygenation of tissue 510 may be monitored using sensing device 500 with optical sensor remaining within the lumen 518 of blood vessel 512. When multiple light emitting and/or detecting portions are included in sensor 502 to allow different emitting-to-detecting pairs and spacings to be selected, and thus different optical pathways to be selected, tissue oxygenation monitoring may be performed at different depths within tissue volume 510. In some embodiments, the tissue volume of interest may be the wall of blood vessel 512.

In one embodiment, blood vessel 512 is a renal vein and tissue volume 510 corresponds to a portion of a patient's kidneys. Method 340 may be used to monitor for tissue hypoxia in the kidney for detecting or predicting the onset of renal failure. Renal failure is often underdiagnosed and can be an important prognostic indicator in heart failure patients. Renal failure also occurs with diabetes and hypertension. Renal failure is associated with prolonged hospital stays and higher mortality. By detecting or predicting hypoxia in kidney tissue, early medical intervention may be taken to reduce hospitalization and mortality caused by renal failure associated with these diseases.

With regard to method 340 of FIG. 8, when tissue hypoxia is detected or predicted in a kidney at block 360, a patient or physician alarm may be generated and/or a device delivered therapy may be initiated or adjusted at block 372. For example, cardiac resynchronization therapy (CRT) or another cardiac pacing, nerve stimulation, or cardiac drug therapy may be administered in a heart failure patient to improve cardiac output in an attempt to improve kidney perfusion.

In another embodiment, vessel 512 may be a vessel of the lower leg used to monitor tissue oxygenation in a diabetic patient. Poor perfusion in the limbs in diabetic patients is a common cause of lower limb amputation. By detecting impaired tissue oxygenation early in a diabetic patient, medical intervention to improve limb perfusion may be taken to preclude amputation. As such, method 340 of FIG. 8 may be used with a transvenous sensing device 500 for detecting/predicting tissue hypoxia in the lower limb (or another extremity) of a diabetic patient.

Figure 10:
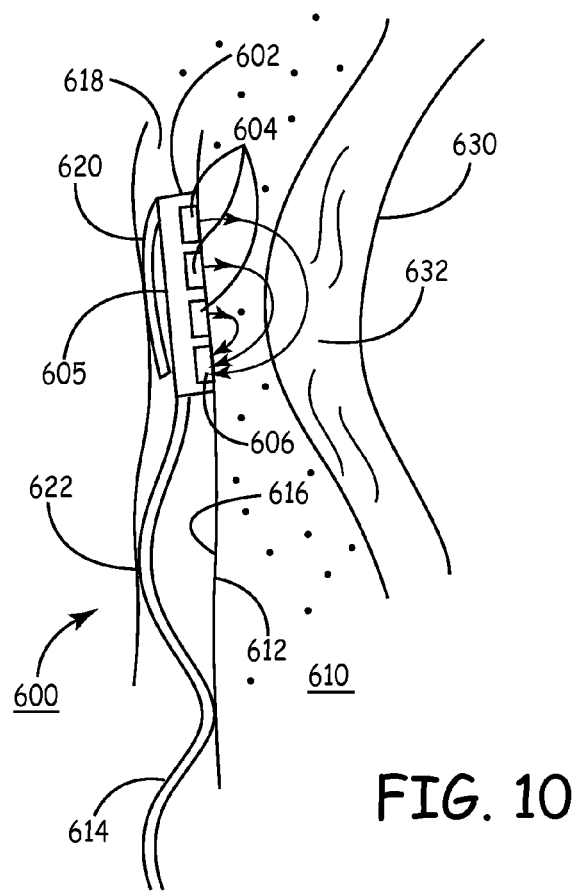
FIG. 10 is a schematic view of an optical sensing device including an elongated lead body and an optical sensor provided at a distal end of the lead body.

FIG. 10 is a schematic view of an optical sensing device 600 including an elongated lead body 614 and an optical sensor 602 provided at a distal end of the lead body 614. An extendable tine 620 is shown extending from a back side 605 of sensor 602. Tine 620 may be embodied as a flexible tine that is preformed to extend radially outward from sensor 602 toward the inner vessel wall 616 opposite the orientation of the sensor emitting and detecting portions 604 and 606. In this way, tine 620 will urge the emitting and detecting portions against the inner vessel wall 616 to allow the sensor 602 to "look out" from the vessel 612. Additionally or alternatively to tine 620, lead body 614 may include preformed curves 622, for example an S-shaped curve as shown, to urge emitting and detecting portions 604 and 606 against inner wall 616.

Optical sensor 602 includes multiple light emitting portions 604 and one light detecting portion 606. Lead 614 carries conductors for delivering control signals to the light emitting portions 604 and for carrying sensor output signals from light detecting portion 606 to an associated implantable medical device, such as IMD 10 shown in FIG. 1. The multiple light emitting portions 604 may be selectively operated to allow detection of light scattered by different tissue volumes encompassed by different optical pathways between the emitting portions 604 and the detecting portion 606. The multiple pathways illustrated by curved arrows will extend different depths into the adjacent tissue 610.

In some embodiments, sensing device 600 may be advanced within a vein 612 to a position adjacent to an artery 630. By properly selecting an emitting portion 604 that results in an optical pathway, i.e. measurement volume, that includes arterial blood 632 flowing in the arterial lumen, arterial $O_2$Sat and HbT may be monitored. Thus transvenous placement of sensing device 600 may allow $O_2$Sat and HbT measurements in an adjacent tissue 610 and/or in an adjacent arterial blood volume 632. Oxygenation measurements obtained for a measurement volume that includes arterial block 632 may provide reference arterial $O_2$Sat measurements for detecting hypoxemia and detecting or predicting tissue hypoxia as generally described in conjunction with FIG. 8.

It is recognized that either of sensing devices 500 and 600 may be provided without a mechanism that holds the sensor windows against the vessel wall such that $O_2Sat$ and HbT measurements may be made along an optical pathway that includes a volume of blood within the vessel lumen. When measurements within a volume of venous or arterial blood are desired using an intravascular device, the orientation of the emitting and detecting portions may be adjusted to direct the optical pathway within the blood volume instead of out of the vessel. It is further contemplated that a mechanism deployed to hold the sensor against the inner surface of the vessel wall may be positioned in a second position that does not hold the sensor against the vein wall. For example, tine 620 or other extendable fixation device may be retracted or an inflatable balloon may be deflated to allow the sensor to move away from the inner wall 616 for performing $O_2Sat$ and HbT measurements within a venous blood volume. The mechanism may then be deployed into a first position that does hold the sensor against the vein wall to allow measurements in tissue adjacent to the vein 612.

Figure 11A:
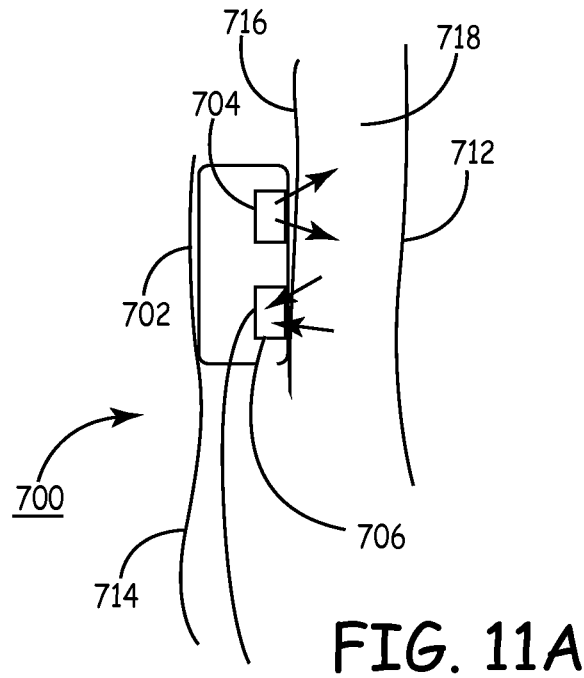
FIG. 11A is a schematic view of an optical sensing device including a sensor coupled to the distal end of a lead.

FIG. 11A is a schematic view of an optical sensing device 700 including a sensor 702 coupled to the distal end of a lead 714 for measuring $O_2Sat$ and HbT in a blood volume. The distal end of sensing device 700 may be advanced to an implant site adjacent to a blood vessel 712, which may be a vein or artery, with emitting and detecting portions 704 and 706 placed in very close proximity or in direct contact with the outer wall 716 of blood vessel 712. Emitting and detecting portions 704 and 706 are configured to "look into" vessel 712, through vessel wall 716. Sensor 702 may be held in position by sutures, active or passive fixation members, or other fixation methods. Light emitted by emitting portion 704 will be scattered by the blood flowing through vessel lumen 718. Remitted light detected by detecting portion 706 allows computation of $O_2Sat$ and HbT that strongly correlates to the $O_2Sat$ and HbT of the respective arterial or venous blood. While some contribution from any intervening tissue, including the vessel wall, may influence the $O_2Sat$ and HbT measurements, proper selection of emitting-to-detecting portion spacing will allow a majority of the optical pathway to extend within the blood volume, making the $O_2Sat$ and HbT measurements more sensitive to changes in the blood than changes in any intervening tissue. Thus $O_2Sat$ and HbT of venous or arterial blood may be monitored using an extravascular optical sensor 702.

Figure 11B:
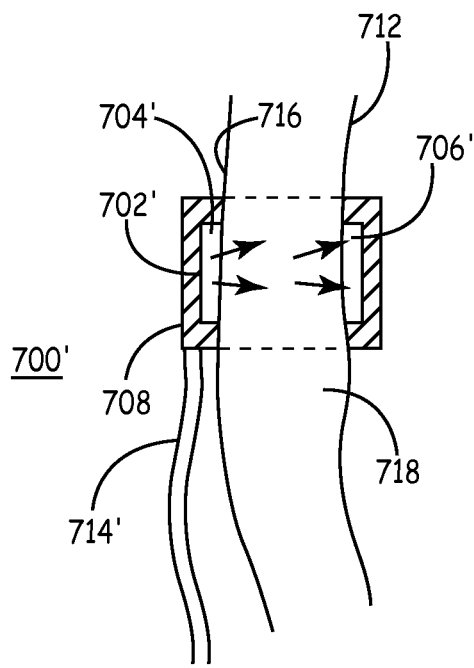
FIG. 11B is a schematic view of an alternative embodiment of an optical sensing device.

FIG. 11B is a schematic view of an alternative embodiment of an optical sensing device 700' used for monitoring $O_2Sat$ and HbT in an arterial or venous blood volume. Device 700' includes an optical sensor 702' mounted to a cuff 708 coupled to a distal end of a lead body 714'. In this embodiment, cuff 708 encircles at least a portion of the vessel 712 thereby positioning the emitting portion 704' and the detecting portion 706' in close proximity or directly against the vessel wall 716 and oriented to emit light into and detect light scattered by the blood volume flowing in lumen 718. The detecting portion 706' may be located along cuff 708 opposite the emitting portion 704', as shown in FIG. 11B. This arrangement positions the detecting portion 706' in facing opposition to emitting portion 704' and thus light signals transmitted through the blood volume will be measured. As shown, detection portion 706' is at approximately 180 degrees from the emitting portion 704'. The detecting and emitting portion may be positioned at any other radial angle with respect to one another and relative to a central axis of the vessel 712.

Figure 12:
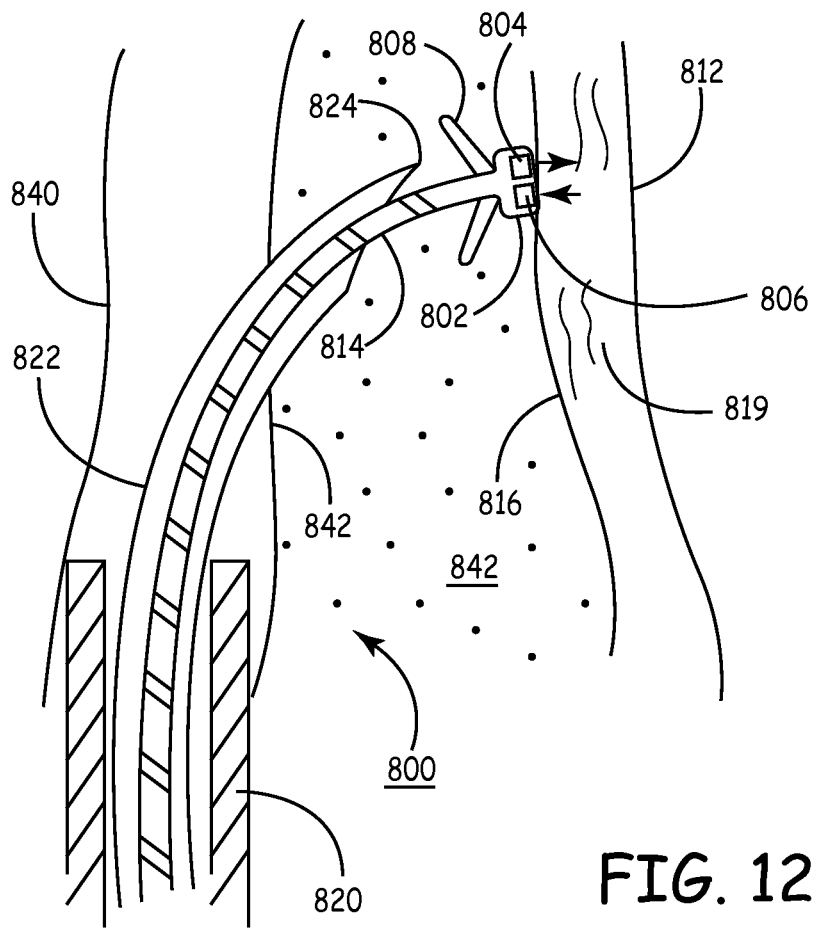
FIG. 12 is a schematic view of yet another embodiment of an optical sensing device.

FIG. 12 is a schematic view of yet another embodiment of sensing device 800 for monitoring $O_2Sat$ and HbT in a blood-perfused tissue or in an arterial or venous blood volume. Sensing device 800 includes an optical sensor 802 coupled to the distal end of lead body 814. Sensing device 800 is sized to be advanced through a hollow needle 822. Hollow needle 822 is provided with a sharpened tip for puncturing through vein wall 842 at a desired puncture site. Hollow needle 822 may be advanced through vein 840 to a puncture site through a hollow delivery catheter 820. Sharpened distal tip 824 is then advanced through vein wall 840. Sensing device 800 is advanced through hollow needle 822 and out distal tip 824 to an extravascular location.

Optical sensor 802 may be positioned within blood perfused tissue 842 adjacent to vein 840 or advanced near or in direct contact with an adjacent artery 812 for monitoring arterial $O_2Sat$ and HbT. Optical sensor 802 may be provided with flexible tines 808 or other fixation mechanisms to promote fixation of sensor 802 within the tissue 842. Hollow needle 822 and delivery catheter 820 may then be removed leaving sensing device 800 in place for monitoring tissue oxygenation in adjacent tissue 842 or artery 812.

Figure 13:
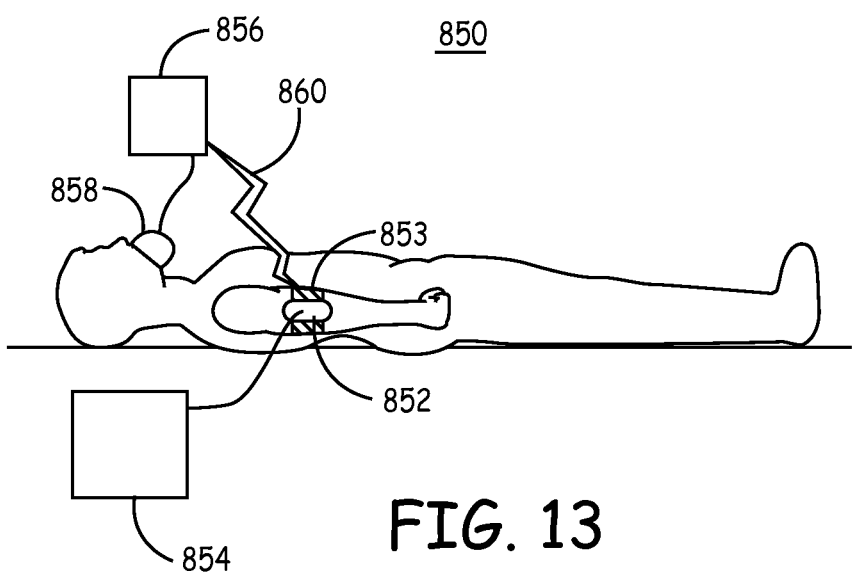
FIG. 13 is a schematic diagram of an external monitoring system for use in monitoring tissue oxygenation.

FIG. 13 is a schematic diagram of an external monitoring system 850 for use in monitoring tissue oxygenation. An optical sensor 852 is shown positioned on a patient's arm for monitoring tissue oxygenation. Sensor 852 includes light emitting and detecting portions (not shown in FIG. 13) as described previously and control circuitry for operating light source(s) and light detector(s). Sensor 852 is shown coupled to an external monitor 854 which may receive optical signals from sensor 852 and process the signals to compute $O_2Sat$ and HbT. Computed measures may be displayed or stored in memory included in monitor 854 for use in determining fluctuations or trends in oxygenation measurements.

The external sensor 852 is shown stably positioned on the patient's arm using a cuff 853 but an adhesive patch or other methods may be used for securing the sensor 852 in a stable position. Sensor 852 may include a power source (battery), processor, control circuitry, memory, wireless telemetry circuitry and other circuitry that enables sensor 852 to operate as a wireless sensor, allowing the patient to be ambulatory without wired connection to external monitor 854. Sensor 852 may transmit oxygenation data wirelessly to external monitor 854 or another implanted or external medical device.

In one embodiment sensor 852 is provided for monitoring tissue oxygenation during a sleep study to evaluate a patient suspected of having sleep apnea or other breathing disorders, such as Cheyne-Stokes breathing. Episodes of predicted or detected tissue hypoxia may be identified using $O_2Sat$ and HbT measurements as generally described in conjunction with method 340 of FIG. 8. Such episodes may be correlated to episodes of apnea. Fluctuations in $O_2Sat$ and HbT may be useful in identifying periods of apnea, hypopnea, and hyperpnea for use in diagnosing a breathing disorder.

The externally-worn sensor 852 may also be used to provide a feedback signal for delivering a therapy using an external therapy delivery device 856. In one embodiment, therapy delivery device delivers a sleep apnea therapy. For example, a patient being treated for sleep apnea may be breathing through a mask 858 coupled to device 856 embodied as a continuous positive airway pressure (CPAP) machine. Sensor 852 may transmit signals to the CPAP machine via a wireless telemetry link 860 (or a hardwired link) to control the pressure applied by the CPAP machine. For example, the $O_2Sat$ and HbT measurements may be used in a feedback algorithm to maintain the pressure applied by device 856 embodied as a CPAP machine at the lowest pressure needed to maintain $O_2Sat$ above a predetermined minimum. High positive pressure can be uncomfortable to the patient so by controlling the pressure in this manner patient discomfort may be reduced.

An adhesive or cuff-mounted sensor 852 may be used in alternative tissue oxygenation monitoring applications wherein a patient applies the sensor 852 to an arm, leg, foot, hand or other body location on a daily, weekly or other periodic basis, or when feeling symptomatic. The sensor may communicate with a home monitor or communication network device to transmit oxygenation measurements to allow chronic monitoring or the tissue oxygenation status. For example, a diabetic patient may apply an external sensor like sensor 852 shown in FIG. 13 on a daily basis to monitor his or her own limb perfusion.

External sensor 852 may be positioned at any core body location, on the head or on an extremity for assessing tissue oxygenation status of a patient and for providing feedback for controlling or assessing the effectiveness of a therapy delivered by external therapy delivery device 856. In one embodiment, external therapy delivery device 856 is an external defibrillator which may include automated cardiopulmonary resuscitation (CPR) delivery. Sensor 852 may provide a tissue oxygenation measurement displayed on external device 856 for feedback to indicate effectiveness of CPR. CPR may be delivered manually by an emergency responder. The tissue oxygenation measurement provides feedback to the emergency responder. Alternatively, the CPR may be delivered by an automated CPR delivery device. The tissue oxygenation measurement may be used as feedback control to allow manual or automatic adjustment of the automated CPR. Sensor 852 may also indicate a restoration of cardiac function following an external defibrillation shock and provide a general indication of the degree or speed of recovery following resuscitation.

FIGS. 14A and 14B illustrate other configurations of external tissue oxygenation sensing devices. In FIG. 14A, an externally worn sensing device 880 includes an optical sensor 884 mounted in a sock or shoe 882 worn by the patient. The device 880 may be worn by a diabetic patient, for example, who would be considered too high risk to undergo surgery for implanting a sensing device. The wearable sensing device 880 may store oxygenation data that is transmitted to a home monitor, programmer, or networked communication device for processing and reporting to a clinician.

FIG. 14B illustrates a sensing device 890 that includes a monitor base 892 and optical sensor 894. Monitor base 890 is shown to include an outline or depression shaped like a foot and may be provided for a patient to place a foot onto for allowing sensor 894 to obtain tissue oxygenation measurements from the patient's foot. In alternative embodiments, a patient may place a digit, hand, lower leg or other extremity against a sensor base unit to thereby enable sensor 894 to obtain tissue oxygenation measurements on a periodic basis.

Thus, a medical device and methods for use have been presented in the foregoing description with reference to specific embodiments. It is appreciated that various modifications to the referenced embodiments may be made without departing from the scope of the invention as set forth in the following claims.

The invention claimed is:

1. A method for monitoring a patient condition in a medical device having an optical sensor, the method comprising:
   advancing the sensor intravascularly to position the sensor along a volume of tissue;
   positioning the sensor along a renal vein, the volume of tissue comprising kidney tissue;
   controlling the optical sensor to emit light comprising at least four spaced-apart light wavelengths;
   detecting light scattered by the volume of tissue, wherein detecting light comprises measuring an optical sensor output signal corresponding to an intensity of the scattered light;
   computing a measure of tissue oxygenation in response to the detected light; and
   detecting hypoxia in the kidney tissue in response to the measurement of tissue oxygenation.

2. The method of claim 1, further comprising computing a measure of total hemoglobin volume fraction using the measure of tissue oxygen saturation.

3. The method of claim 1, further comprising adjusting a therapy in response to the measure of tissue oxygenation.

4. The method of claim 1, further comprising positioning the sensor along an inner vessel wall to orient the sensor to emit light through the vessel wall into the volume of tissue.

5. The method of claim 4, wherein the volume of tissue comprises a volume of arterial blood.

6. The method of claim 1, further comprising positioning the sensor through a vessel wall into tissue adjacent to the vessel wall to orient the sensor to emit light into the volume of tissue.

7. The method of claim 1, further comprising positioning the sensor through a vessel wall to orient the sensor to emit light into a volume of arterial blood.

8. The method of claim 1, further comprising positioning the sensor along a peripheral vein.

9. The method of claim 1, further comprising adjusting a heart failure therapy in response to detecting the tissue hypoxia.

10. The method of claim 1 further comprising positioning the sensor on a patient's skin.

11. The method of claim 10, further comprising delivering a therapy to the patient and adjusting the therapy in response to the tissue oxygenation measurement.

12. The method of claim 11, wherein the therapy comprises cardiopulmonary resuscitation.

13. The method of claim 1, wherein computing the measure of tissue oxygenation comprises:
   computing an attenuation for each of the at least four wavelengths of detected light;
   computing a second derivative with respect to wavelength for at least two intermediate wavelengths of the at least four wavelengths; and
   computing a scaled second derivative of one of the intermediate wavelengths as a ratio of the at least two intermediate wavelengths.

14. A medical device system, comprising:
   a sensor capable of being advanced transvascularly to be positioned along a volume of tissue, the sensor comprising a first combination of a light source and a light detector to emit light into a volume of tissue, to detect light scattered by the volume of tissue, and to generate a first output signal corresponding to an intensity of the detected light, wherein the first combination of a light source and a light detector is capable of being positioned adjacent to kidney tissue, and wherein the monitoring module detects kidney hypoxia in response to the measurement of tissue oxygenation; and
   a control module coupled to the light source to control the light source to emit light comprising at least four spaced-apart light wavelengths; and
   a monitoring module coupled to the light detector to receive the output signal and compute a measure of tissue oxygenation in response to the light detector output signal.

15. The system of claim 14, wherein the monitoring module further computes a measure of total hemoglobin volume fraction using the measure of tissue oxygen saturation.

16. The system of claim 14, wherein the sensor further comprises a second combination of a light source and light detector for detecting light scattered by a volume of arterial blood and providing a second output signal corresponding to an intensity of the detected light scattered by the volume of arterial blood, wherein the monitoring module is coupled to the light detector of the second combination, computes a measure of arterial oxygen saturation in response to the second output signal, and detects tissue hypoxia in response to the measure of arterial oxygen saturation.

17. The system of claim 14, further comprising:
a therapy delivery module; and
a therapy delivery controller coupled to the monitoring module and the therapy delivery module, the therapy delivery controller adjusting a therapy in response to the measure of tissue oxygenation.

18. The system of claim 14, further comprising an elongated electrical lead, wherein the first combination of the light source and the light detector is positioned along the elongated lead.

19. The system of claim 14, wherein the sensor is positioned along an inner vessel wall to orient the light source to emit light through the vessel wall into a volume of tissue adjacent to the vessel wall.

20. The system of claim 14, wherein the first combination of a light source and a light detector is positioned along an outer vessel wall of a vessel to orient the light source to emit light through the outer vessel wall into a lumen of the vessel.

21. The system of claim 20, wherein the light detector is positioned along the outer vessel wall in facing opposition to the light source.

22. The system of claim 14, further comprising a hollow needle having a puncturing distal tip for advancing the needle through a wall of a blood vessel, wherein the first combination of the light source and the light detector are sized to be advanced through the hollow needle into a volume of tissue adjacent to the blood vessel.

23. The system of claim 14, further comprising:
a therapy delivery module; and
a controller coupled to the monitoring module and the therapy delivery module to adjust a therapy in response to detecting the kidney hypoxia.

24. The system of claim 14, wherein computing the measure of tissue oxygen saturation by the monitoring module comprises:
computing an attenuation for each of the at least four wavelengths of detected light;
computing a second derivative with respect to wavelength for at least two intermediate wavelengths of the at least four wavelengths; and
computing a scaled second derivative of one of the intermediate wavelengths as a ratio of the at least two intermediate wavelengths.

25. A medical device system, comprising:
a sensor capable of being advanced transvascularly to be positioned along a volume of tissue, the sensor comprising a first combination of a light source and a light detector to emit light into a volume of tissue, to detect light scattered by the volume of tissue, and to generate a first output signal corresponding to an intensity of the detected light, wherein the first combination of the light source and the light detector are positioned along a patient's skin; and
a control module coupled to the light source to control the light source to emit light comprising at least four spaced-apart light wavelengths; and
a monitoring module coupled to the light detector to receive the output signal and compute a measure of tissue oxygenation in response to the light detector output signal.

26. A non-transitory computer readable medium having computer executable instructions for performing a method for monitoring a patient condition in a medical device having an optical sensor, the method comprising:
advancing the sensor intravascularly to position the sensor along a volume of tissue;
positioning the sensor along a renal vein, the volume of tissue comprising kidney tissue;
controlling the optical sensor to emit light comprising at least four spaced-apart light wavelengths;
detecting light scattered by the volume of tissue, wherein detecting light comprises measuring an optical sensor output signal corresponding to an intensity of the scattered light;
computing a measure of tissue oxygenation in response to the detected light, wherein computing the measure of tissue oxygen saturation by the monitoring module comprises:
computing an attenuation for each of the at least four wavelengths of detected light;
computing a second derivative with respect to wavelength for at least two intermediate wavelengths of the at least four wavelengths; and
computing a scaled second derivative of one of the intermediate wavelengths as a ratio of the at least two intermediate wavelengths; and
detecting hypoxia in the kidney tissue in response to the measurement of tissue oxygenation.

* * * * *